United States Patent [19]

Markowitz et al.

[11] Patent Number: 5,088,488
[45] Date of Patent: Feb. 18, 1992

[54] METHOD AND APPARATUS FOR IMPLEMENTING HISTOGRAM STORAGE AND TREND ANALYSIS IN A MEDICAL STIMULATOR

[75] Inventors: Harold T. Markowitz, Roseville; Ann L. Ledin, Minneapolis, both of Minn.

[73] Assignee: Medtronic, Inc., Minneapolis, Minn.

[21] Appl. No.: 455,646

[22] Filed: Dec. 22, 1989

[51] Int. Cl.⁵ .............................................. A61M 1/362
[52] U.S. Cl. .............................. 128/419 PG; 128/706
[58] Field of Search .................... 128/419 PG, 706

[56] References Cited

U.S. PATENT DOCUMENTS

| | | | |
|---|---|---|---|
| 4,223,678 | 9/1980 | Langer et al. | 128/419 |
| 4,513,743 | 4/1985 | van Arragon et al. | 128/419 PG |
| 4,726,380 | 2/1988 | Vollmann et al. | 128/419 PG |
| 4,827,933 | 5/1989 | Koning et al. | 128/419 PG |
| 4,830,488 | 5/1989 | Heinze et al. | 128/419 PG |
| 4,873,980 | 10/1989 | Schaldach | 128/419 PG |
| 4,884,576 | 12/1989 | Alt | 128/419 PG |

OTHER PUBLICATIONS

A New Concept in Rate Responsive Pacing Using the QT Interval, Vitatext, Oct. 1987.
Legend ® Multiprogrammable Rate Responsive (Activity) Pulse Generator, Medtronic, 1988.
Example Agreement, Legend Implantable Pulse Generator Models 8416, 8417 and 8418.

*Primary Examiner*—William E. Kamm
*Assistant Examiner*—Scott M. Getzow

[57] ABSTRACT

An implantable medical device employing a random access memory for storage of data relating the physiologic condition of the patient in which the device is implanted and/or information related to the functioning of the device. The memory and associated addressing circuitry are reconfigurable to allow for storage and display of information in either a histogram or trend line format.

12 Claims, 17 Drawing Sheets

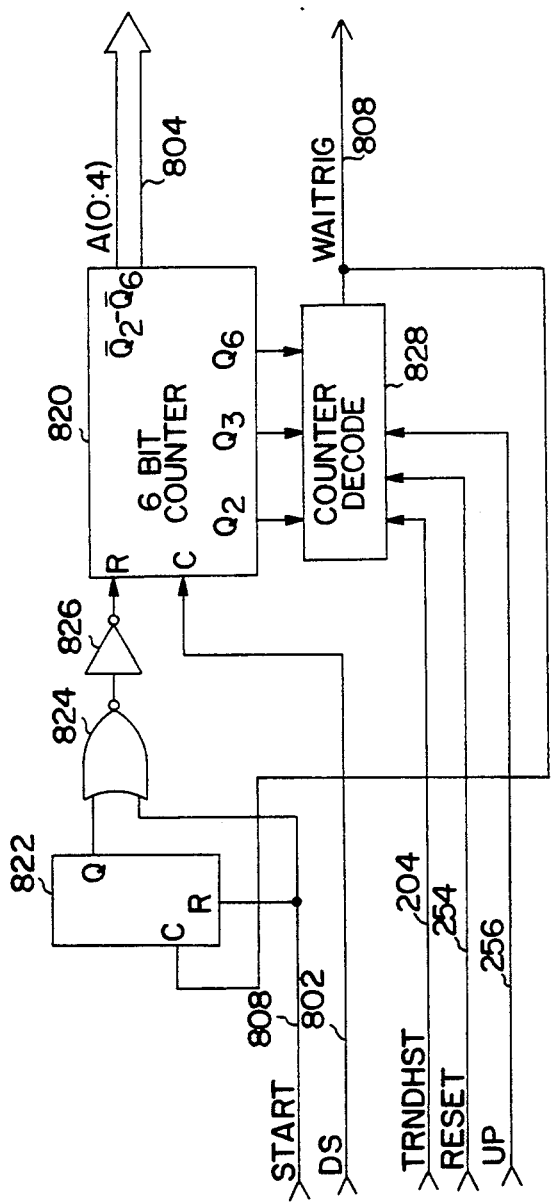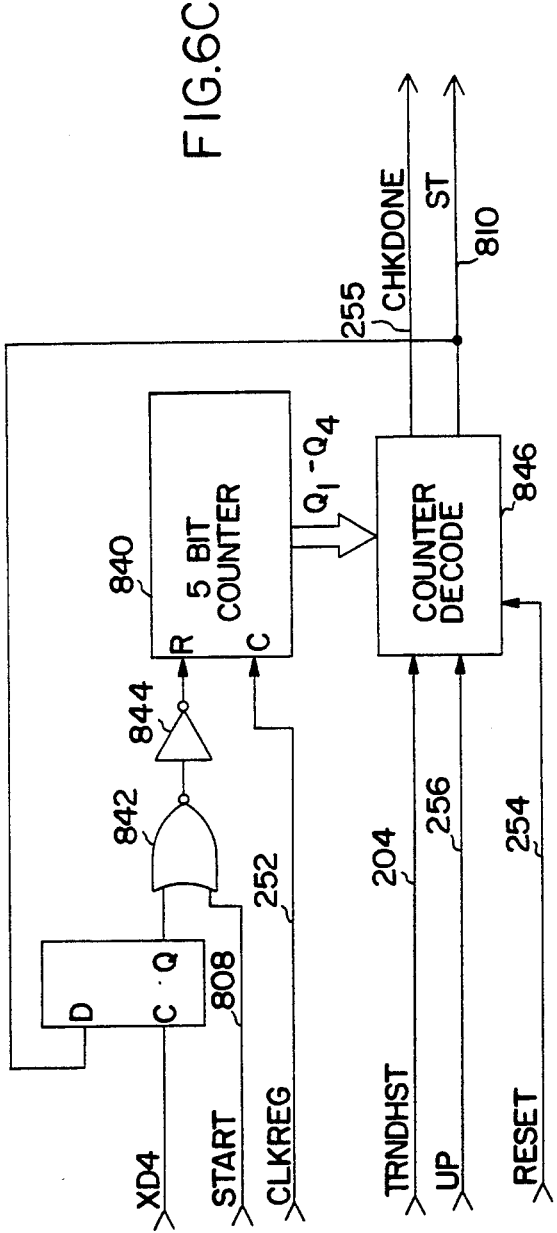

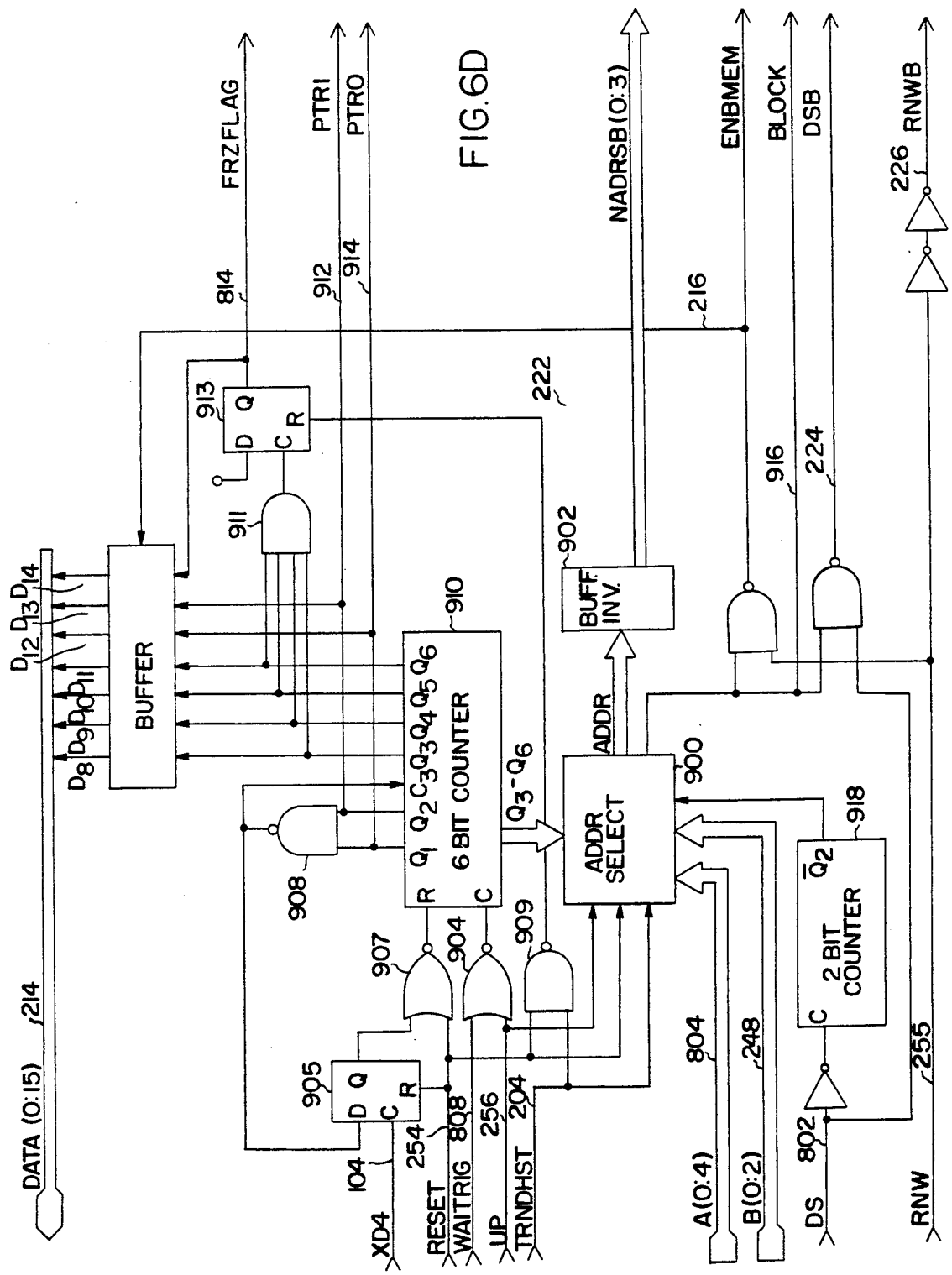

EVENT COUNTERS AT 07:07:11

TELEMETRY VALUES:
SOURCE: HEART RATE
FORMAT: I TREND
TERM:   SHORT
BINS:   STANDARD

| ELAPSED TIME (MIN) | AVG RATE (PPM) | %PACED 0-25-50-75-100 |
|---|---|---|
| .61 | 105 | x (100) |
| 1.12 | 125 | x (100) |
| 2.10 | 65 | x (100) |
| 2.95 | 75 | x (50) |
| 3.46 | 125 | x (100) |
| 3.97 | 125 | x (100) |
| 4.48 | 125 | x (100) |
| 4.99 | 125 | x (100) |
| 5.50 | 125 | x (100) |
| 6.01 | 125 | x (100) |
| 6.57 | 115 | x (50) |
| 7.24 | 95 | x (100) |
| 7.91 | 95 | x (50) |
| 8.66 | 85 | x (100) |
| 9.51 | 75 | x (100) |

FIG. 8a

```
EVENT COUNTERS AT    08:33:48

TELEMETRY VALUES:
SOURCE: SENSED RATE
FORMAT: HISTOGRAM
TERM:   SHORT
BINS:   STANDARD
  RATE      TOTAL     %
  BINS      EVENTS  TOTAL      % PACED
  (PPM)    / TERM  EVENTS    0-25-50-75-100
   <61        0       0      : *
   61-70    179      70      : *
   71-80     12       5      : *
   81-90      3       1      : *
   91-100     6       2      : *
  101-110     8       3      : *
  111-120    17       7      : *
   >120      32      12      : *
  TOTAL     257
```

FIG.8b

METHOD AND APPARATUS FOR IMPLEMENTING HISTOGRAM STORAGE AND TREND ANALYSIS IN A MEDICAL STIMULATOR

CROSS REFERENCE TO COMMONLY ASSIGNED COPENDING APPLICATION

Reference is made to U.S. patent application Ser. No. 455,717, for a "METHOD AND APPARATUS FOR IMPLEMENTING ACTIVITY SENSING IN A PULSE GENERATOR", filed as of the date of this application by Sivula et al.

BACKGROUND OF THE INVENTION

This invention generally relates to medical stimulators and monitors, and more specifically relates to implantable stimulators and monitors such as cardiac pacemakers and neuro stimulators.

In recent years, it has become desirable for implantable stimulators to maintain some form of record of the patient's condition and/or the function of the stimulator for later display and interpretation. Data storage algorithms in implantable stimulators have generally fallen into two classes, short recordings of electrophysiologic parameters, such as EKG strips, and longer term event storage with data stored and displayed in the form of histograms. Storage of short EKG segments illustrating the function of an implantable stimulator are disclosed in U.S. Pat. No. 4,223,678, issued to Langer et al. Histogram type event storage is disclosed in U.S. Pat. No. 4,513,743, issued to VanArragon et al.

SUMMARY OF THE INVENTION

The present invention employs an event counting and storage apparatus which can function in either of two modes, including histogram storage and trend line storage. The specific embodiment disclosed is an implantable cardiac pacemaker which generates pacing pulses at a rate determined by a sensor which is responsive to the metabolic demand for oxygenated blood. The output of this sensor is used to regulate the pacemaker's escape interval. The output of this sensor is used to regulate the pacemaker's escape interval.

The pacemaker includes event counters which track the occurrence of event markers triggered in response to the sensing of natural heart activity, the generation of pacing pulses, and the expiration of the sensor controlled pacemaker escape interval. The particular events to be counted are selectable by means of an external programmer. The events are counted by the pacemaker with a view towards keeping a record of the rate of their occurrence. Information with regard to the rate of event occurrence is stored in one of two formats, referred to hereafter as "trend analysis" and "histogram storage". Election between these two formats is accomplished by means of an external programmer.

If histogram storage is selected, the event counters are enabled to count up to a predetermined number of events, and the number of events is compared to the time period over which the events were counted to derive an average rate value. Each average rate value is categorized as falling into one of eight rate ranges, hereafter referred to as rate "bins". In addition, the pacemaker keeps track of which of the events counted were due to the generation of a stimulus pulse, and provides a calculation as to their percentage of the total number of counted events. This value is referred to as the "percent paced" value. Each percent paced value is likewise assigned to one of eight rate bins corresponding to the rate bin for the concurrently calculated average rate value. Thus, in histogram storage mode, the pacemaker has 16 storage bins, divided into eight rate ranges. For each rate range, there are two storage bins, one containing a running count of the number of average rate values falling within that rate range, the other containing a valve reflecting the percentage of events falling within that rate range due to the generation of pacing pulses. Counting and storage of average rate values and percentage paced values continues until one of the storage bins is completely full, at which point further storage is inhibited.

If trend analysis is elected, counting and calculation of average rate values is performed as in histogram storage, although typically with a greater number of events counted for each average. In this mode of data storage, the forty-eight calculated average rate values are stored in sequence along with the corresponding percentage paced value. This information thus provides a time ordered record of average event rate and percentage of paced events.

Because the average event rate corresponds to the average heart rate of the patient, the event counters are believed to provide a useful diagnostic tool to the physician. In the present invention, the particular events to be counted, the term over which the events are counted before averaging (number of events counted before averaging), and the definition of the various rate bins are all selectable by the physician so that the data collection may be tailored to the specific needs of the physician.

The present invention is particularly adapted to implementation in an implanted stimulator, as it allows either histogram storage or trend analysis using a memory of limited capacity, which may be reconfigured depending upon the particular storage format chosen. In the specific embodiment disclosed, the memory employed for event counter storage is a 16×16 bit random access memory. In histogram storage mode, the 16 addresses correspond to the 16 storage bins, eight average rate value bins, eight percentage paced bins. When trend analysis is elected, each of the 16 addresses in the memory holds three sequential 5-bit words, each 5-bit word corresponding to the calculated average rate value and the percentage paced value for one counting cycle. Within each 5-bit word, the first three bits reflect the calculated average rate value and the last two bits reflect the concurrently calculated percentage paced value.

The invention is particularly economical in its use of electronic circuitry, in that it makes multiple use of the various functional components of the event counting circuitry, adapting them to somewhat different uses depending upon the particular data storage format selected.

BRIEF DESCRIPTION OF THE DRAWINGS

FIGS. 6A, 6B, 6C and 6D illustrate the sequence/control circuitry illustrated in FIG. 2B.

FIGS. 8A, 8B, 8C and 8D illustrate appropriate display formats for the information stored by the event counter circuitry illustrated in the figures above.

DETAILED DESCRIPTION OF THE INVENTION

Figure 1:
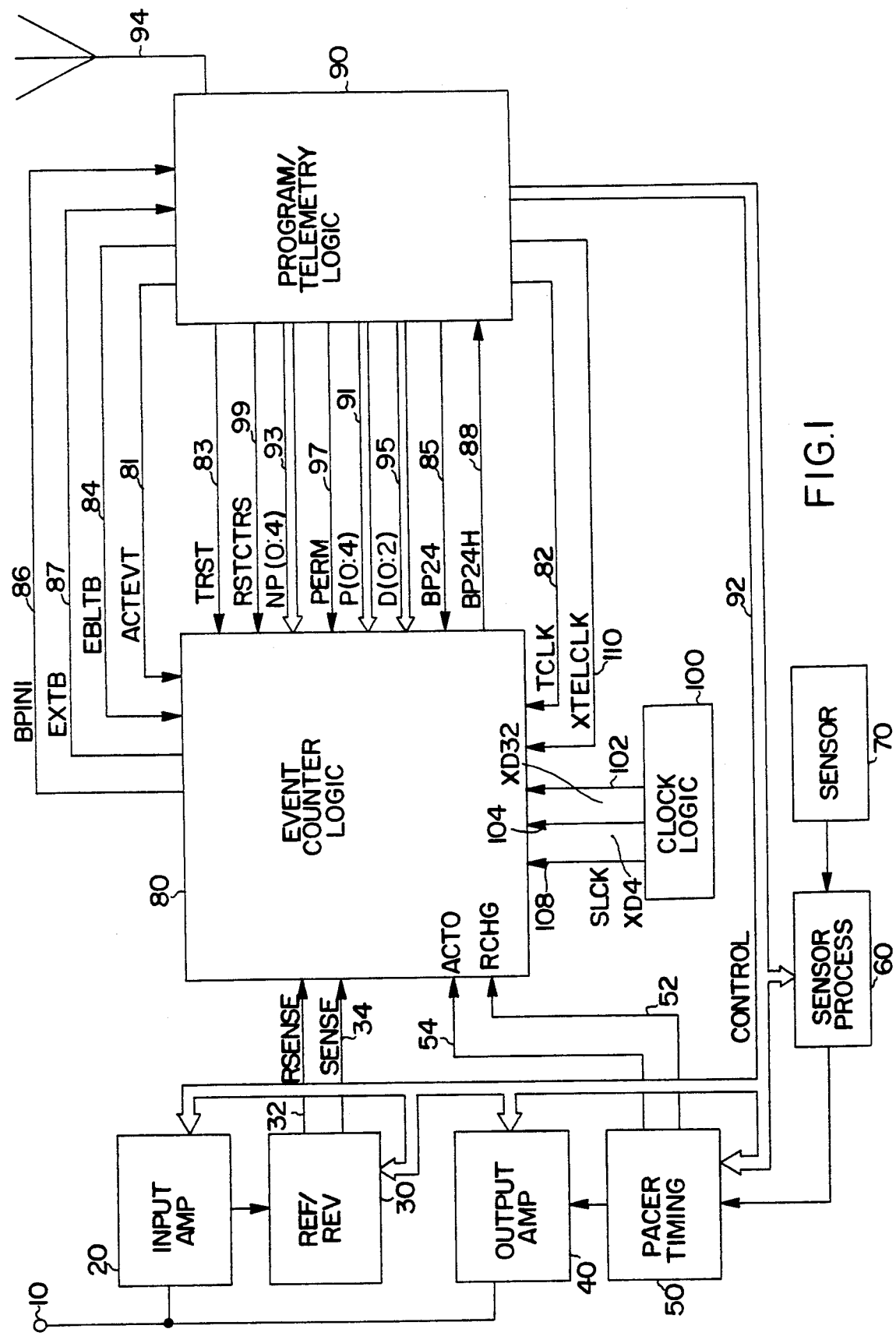
FIG. 1 is a block diagram of a sensor regulated cardiac pacemaker according to the state of the art, including the improved event counter circuitry of the present invention.

FIG. 1 is a functional block diagram illustrating the improved event counter circuitry of the present invention and its relationship to an implantable cardiac pacemaker. The pacemaker is coupled to the heart by means of a stimulation/sensing electrode 10. Electrical signals indicative of the contraction of the heart are picked up by electrode 10, and are filtered and amplified by input amplifier 20. Signals indicative of the occurrence of natural heart activity are passed through to the reversion/refractory circuit 30, which provides two of the event signals employed by the event counter logic 80. One of these event markers takes the form of a signal on RSENSE line 32, and is indicative of the occurrence of natural electrical activity in the heart during the refractory period defined by refractory/reversion circuitry 30. The second event marker takes the form of a signal on SENSE line 34, which indicates the occurrence of natural electrical activity in the heart outside of the refractory period defined by refractory/reversion circuitry 30. These signals are hereafter referred to as "R-sense" and "sense" signals.

Stimulation pulses are delivered to the electrode 10 by output amplifier 40, under control of pacer timing logic 50, which determines the escape interval for the pacemaker. Pacer timing logic 50 also provides two event marker signals to the event counter logic 80, including the signal on RCHG line 52, indicative of the triggering of the output amplifier 40 and the signal on ACTO line 54, indicative of the time out of the escape interval determined by sensor processing circuitry 60. These signals are hereafter referred to as the "RCHG" and "ACTO" signals. In modern pacemakers, the timing and characteristics of stimulation pulses are determined by a stored program, located in program/telemetry logic 90, communicated to pacer timing logic 50 by means of control bus 92. In the illustrated embodiment, a sensor 70 responsive to physiologic demand for oxygenated blood provides a measurement signal to sensor processing circuitry 60 which may be used to vary the escape interval of the pacemaker.

Operation of the pacemaker is controlled by means of information stored in program/telemetry logic 90, which includes storage registers which hold information regarding the various operative functions of the pacemaker. Data is entered into program/telemetry logic 90 by means of antenna 94, which receives signals from an external programmer. While the control bus 92 is illustrated only as coupled to the pacer timing logic 50, it should be understood that in most modern pacemakers, the characteristics of the output amplifier 40, input amplifier 20 and reversion/refractory circuitry 30 are also under control of the information stored in the program/telemetry logic 90.

The above described portion of the pacemaker may be borrowed from any currently available sensor regulated cardiac pacemaker, provided that it is capable of providing appropriate signals to event counter logic 80 and responding to the signals from event counter logic 80. Examples of appropriate program/telemetry logic may be found in U.S. Pat. No. 4,257,423, issued to McDonald et al on Mar. 24, 1981, and U.S. Pat. No. 4,566,063 issued to Thompson et al on Dec. 31, 1985, both of which are hereby incorporated by reference in their entirety. U.S. Pat. No. 4,476,868, issued to Thompson on Oct. 16, 1984 and U.S. Pat. No. 4,379,459, issued to Stein on Apr. 12, 1983 which disclose input and output amplifiers, associated refractory and reversion circuits and pacer timing circuitry, and U.S. Pat. No. 4,485,813, issued to Anderson and Brumwell which discloses an appropriate sensor and sensor processing circuitry for varying the pacing rate are all also incorporated herein by reference in their entirety. However, the specific embodiments of these various functional blocks of the pacemaker are not believed critical to the present invention. Indeed, the disclosed improved event counter circuitry may be practiced in conjunction with any imlantable stimulator or monitoring device which may be used to provide event related signals of interest to the physician, and which is provided with programming and telemetry logic enabling receipt and storage of programming signals and transmission of the information stored by the event counter logic. As such, FIG. 1 should be considered an example of one particular embodiment of the present invention, and should not be considered as limiting. It is believed that one of skill in the art would readily apprehend numerous other appropriate forms of medical stimulators in which to employ the improved event counter circuitry.

Clock block 100 provides clock signals to the event counter logic to assist it in performing its timing and counting functions. These include a clock signal on XD32 line 102, hereafter referred to as the XD32 clock, the clock signal on XD4 line 108, hereafter referred to as the XD4 clock, and the clock signal on SLCK1 line 108, hereafter referred to as the slow clock signal.

Program telemetry logic 90 provides a variety of information and trigger signals to the event counter logic 80. These signals are generated in two contexts, programming of the event counter logic, and telemetry of the information in the event counter logic out to the external programmer. Telemetry of the event counter logic is initiated by the program/telemetry logic, and the telemetry function is controlled by ACTEVT line 81, which is low during event counter telemetry, TCLK line 82 and XTELCLK line 110 which serves as a telemetry clock for clocking out stored information from event counter logic 80, TRST line 83, which resets certain telemetry functions within event counter logic 80 and BP24 line 85, which initiates telemetry of stored information within event counter logic 80 with regard to the programmed event counter format. Event counter logic 80 provides signals to programmed/telemetry logic related to the telemetry of information, including telemetry bus (EXTB) 87 which is a serial telemetry bus carrying information from event counter logic 80, BPIN1 line 86, which indicates the cessation of telemetry from event counter logic 80, BP24H line 88 which indicates cessation of telemetry of programmed event counter parameters, such as format and term, and PSHFRST line which 89 resets the program telemetry logic 90, clearing the request for event counter telemetry from program/telemetry logic 90 after cessation of event counter logic telemetry.

Event counter logic 80 includes an internal memory for storage of programmed parameters related to event counter function. This includes information as to the selection of histogram or trend analysis, the number of events counted per calculated average rate, and the particular events to be counted. These include two 5-bit parameter buses P bus 91 and NP bus 93, which indicate the particular parameter to be programmed. Data concerning the selected value of the parameter to be programmed is available on D bus 95. PERM line 97 is strobed high during programming, and is also used to reset the event counter circuitry.

The event counter logic 80 may be also reset under control of program/telemetry logic 90 by means of a signal on RSTCNTRS line 99, which reinitializes the event counter logic. The operation of these functional blocks and the significance of the signals on the various lines discussed above is dealt with in substantially more detail below.

Figure 2A:
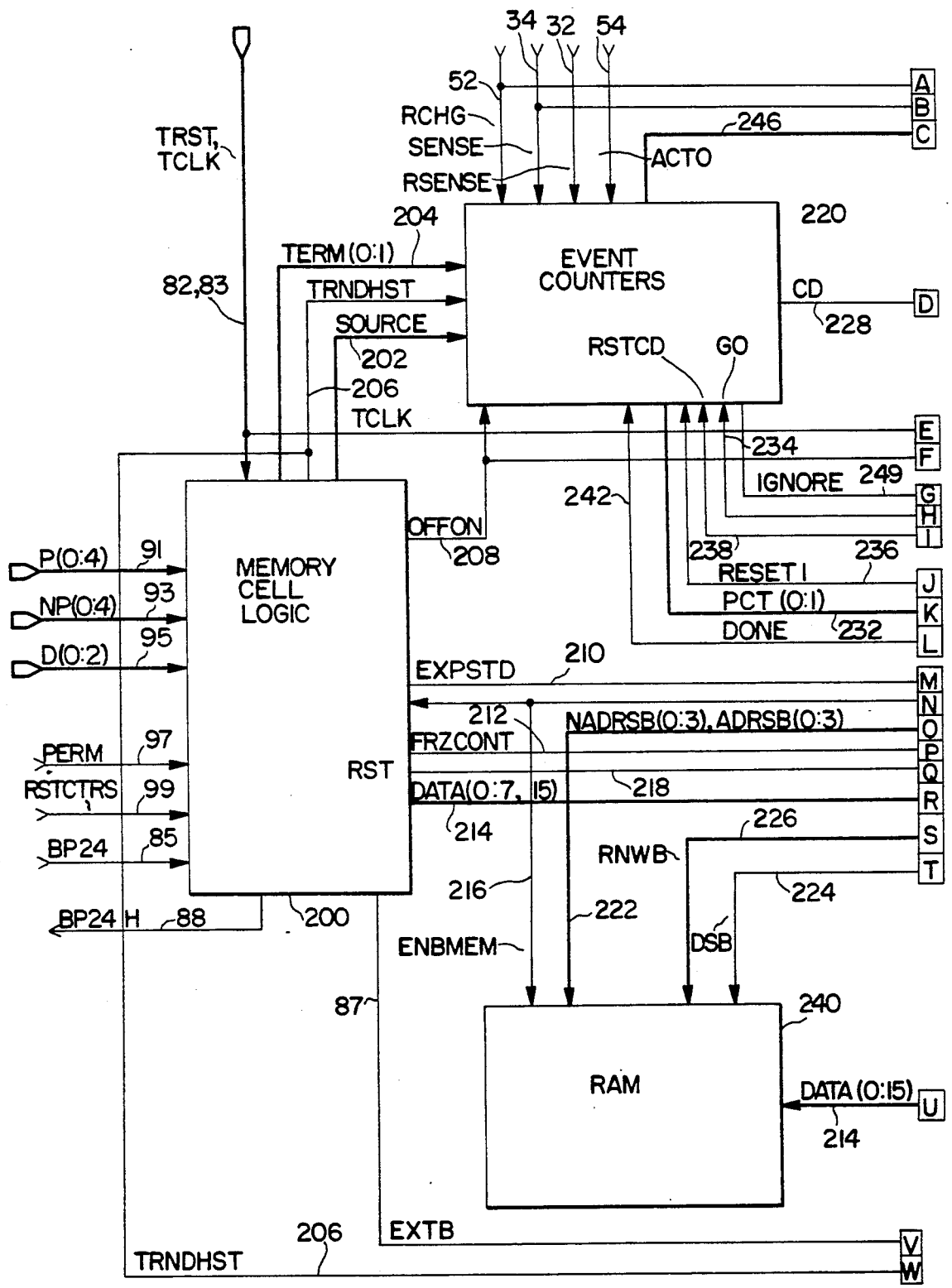
FIGS. 2A and 2B are a schematic block diagram illustrating the event counter circuitry of FIG. 1.
Figure 2B:
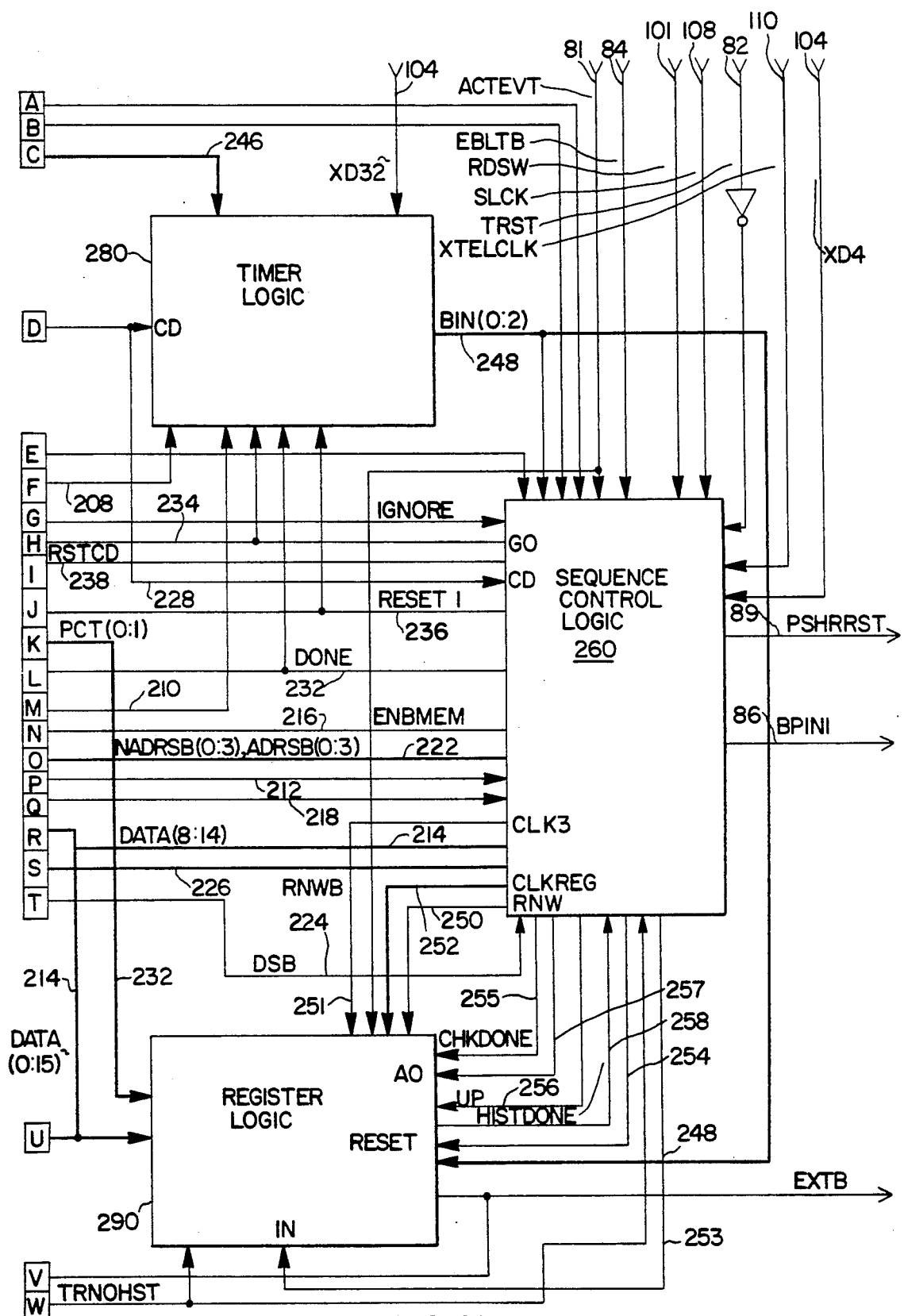

FIGS. 2A and 2B are functional block diagrams of the circuitry within event counter logic 80. Inputs to and outputs from the event counter logic correspond to those in FIG. 1. In addition, interconnects between the various functional blocks are illustrated.

The memory cell logic 200 functions as the memory for all programmed event counter parameters, and includes nine memory cells. Three memory cells store information relating to the selected events to be counted, selecting between RCHG signals, SENSE signals, RSENSE signals and ACTO signals. This information is available to the event counters 220 via a 3-bit SOURCE bus 202. Two memory cells are allocated to storing the desired number of events to be counted prior to calculating an average rate value and a corresponding percent paced value. This information is available on 2-bit TERM bus 204. One memory cell is allocated to storing the physicians' selection between trend analysis and histogram storage. This information is available on TRNDHST line 206. One memory cell is used to turn the event counter function on or off. This information is available on OFFON line 208. One memory cell is allocated to the selection between a regular or expanded set of rate bin selections. This information is available on EXPSTD line 210. One memory cell controls frame of the 1 trend analysis, i.e., whether it retains the initial 48 averaged rates calculated after initiation of trend analysis (initial trend) or to the 48 most recent averaged rates (final trend). This information is available on FRZCONT line 212, which controls whether trend analysis ceases when the random access memory 240 is initially filled, or whether trend analysis will continue, with more recent averaged rate values being written over the oldest average rate values.

The data stored in the memory cell logic 200 is available on lines 0-7 and 15 of DATA bus 214, enabled in response to a high signal on ENBMEM line 216. The information stored in the memory cells is available in serial form on external telemetry bus line EXTB 87.

Memory cell logic 200 also provides a reset signal on RST line 218 in response to an instruction to reset the event counters from the programmer, indicated by a signal on RSTCTRS line 99 or in response to the reprogramming of any stored parameter within the memory cell with the exception of frame selection.

Random access memory 240 stores the information generated by the event counter circuitry 220. RAM 240 takes the form of a 16×16 bit random access memory with 16 addresses. Writing to and reading from random access memory is disabled by a high signal on ENBMEM line 216. Addressing of the RAM is controlled by bus 222, which is an 8-bit bus containing four bits representative of the address (ADRSB(0:3) and four bits representative of the inverse of the address (NADRSB(0:3). Data is provided to the random access memory via DATA bus 214. Information is written into or read out of random access memory in response to a data strobe signal on DSB line 224, with the choice between reading into the RAM and out of the RAM made via RNWB (Read not Write) line 226.

Event counter 220 performs the event counting and percentage paced calculations discussed above. Each time the event counter has counted the number of events specified by the information on TERM bus 204, CD line 228 goes high indicating that the counter is done. The calculated percent paced value is available on 2-bit PCT bus 232. The event counters are reset by RESET1 line 236, which resets all stages of the event counters. The final stage of the event counters is reset by RSTCD line 238. Event counting is initiated by a signal on GO line 234, and is disabled by a high signal on DONE line 242. If only sensed events (SENSE and RSENSE) signals are to be counted, IGNORE line 244 will go high each time a paced event (RCHG signal) occurs. This in turn will trigger a reset signal on RESET1 line 236 via sequence control logic 260. This assures that the series of events counted and averaged is limited to only natural heartbeats, so that the resulting stored information reflects only the intrinsic heart activity of the patient.

Event counter 220 also contains logic for decoding the number of events to be counted during each event counter cycle (for each calculated average rate value). This is available on a 5-bit bus 246, which includes five individual data lines, only one which will carry a high logic signal indicative of the selection of long term trend analysis (LTRND), long term histogram or medium term trend analysis (LHORMT), short term trend analysis (STRND), medium term histogram storage (MHIST), or short term histogram storage (SHIST). The information on data bus 246 is provided to timer logic 280. Timer logic 280, like event counters 220, is disabled by a high signal OFFON on line 208, reset by a high signal on RESET1 line 236, initiated by a high signal on GO line 234, and turned off by a high signal on DONE line 242. Timer logic 280 determines the time interval between reset of the event counter 220 and the counting of the number of events specified by TERM bus 204, as indicated by a high signal on CD line 228. This allows for timer logic 280 to determine the average rate of event occurrences. The calculated average rate value is sorted into one of 8 rate bins, each extending over a predetermined range of rates. The average rate value is expressed by an identification of which of the various rate bins the average rate falls into and is available from timer logic 280 on 3-three bit BIN bus 248. In the trend analysis mode, this information is stored in conjunction with percent pace code on PCT bus 232 for the corresponding series of events. In the histogram storage mode, the value on BIN bus 248 is used to determine the address of the random access memory to be incremented. Selection of bin ranges is accomplished via EXPSTD line 210. Two series of rate bins extending from <60 beats per minute to >120 beats per minute (low signal on EXPSTD line 210) or from <60 beats to >220 beats per minute (EXPSTD line 210 set high) are available.

The function of register block 290 is to operate on data after being read from RAM 240 and before being written back into RAM 240. Data is read from the RAM onto DATA bus 214 and parallel loaded into the register block, shifted or incremented and written back into the random access memory 240. This series of events is referred to as the "basic pattern" and is common to all modes of operation. These functions are performed in conjunction with both the trend analysis and histogram storage mode and are discussed in more detail below.

Percentage paced calculations performed by the event counter 220 are provided to the register 290 via PCT bus 232. Information regarding the average event rate (bin code) is available on bin bus 248. This information is loaded into the RAM via the register logic 290, if trend analysis has been selected. Reading to and writing from the shift register is controlled by RNW line 250. Clocking of the shift register is accomplished by CLKREG line 252, and the register is reset via RESET line 254. Functioning of the shift register during telemetry is controlled via ACTEVT line 81 and UP line 256, from sequence control logic 260, which also provides additional control signals on CHKDONE line 255, AO line 257, and HISTDONE line 258. The functions of these various control lines and their interrelation between the register logic 300 and the sequence control logic 260 is discussed in more detail below.

Sequence/control logic 260 controls the basic operation of the event counter circuitry. This operation can be broken down into four basic types of sequences, including a reset sequence, an uplink sequence, trend analysis update, and histogram update. Only one of these sequences is active at any given time. The four types of sequences share the basic pattern of operation. The differences between sequences lie in the number of times the basic pattern of operation is repeated for each sequence and the shifting or incrementation of the data while in the shift register Control of these sequences is accomplished by sequence control logic 260, under control of the program stored in the program/telemetry logic 90 (FIG. 1) and the memory cells block 200 of the event counter logic. Inputs to sequence control logic 260 include IGNORE line 244 from event counters 220 which, as discussed above, triggers a reset signal on RESET1 line 236, CD line 228 indicating counting of the number of events specified by the information on TERM bus 204, FRZCONT line 212 and RST line 218 from memory cells 200, RCHG line 52, SENSE line 34, and the other inputs described in conjunction with FIG. 1 from the program/telemetry logic 90. Outputs from the sequence control logic include DONE line 232 indicating termination histogram storage or trend analysis, RESET1 line 236, RSTCD line 238, ENMBMEM line 216, UP line 256, CHKDONE line 255 and the buffered data strobe on DSB line 224.

Sequence control logic 260 also controls the addressing functions for random access memory 240 via 8-bit bus 222, provides data to lines 8-14 of DATA bus 214, and controls the state of the buffered read not write (RNWB) line 226. Sequence control logic also controls the operation of register logic 300 by control of the register clock on line 252, the read not write (RNW) line 250, and the CHKDONE line 255, AO line 257, UP line 256 and RESET line 254.

While the specific functions of the sequence control logic 260 are set forth in more detail below, the general operation of the four available sequences (reset, uplink, histogram update and trend update) are as follows.

A reset sequence is initiated by either a programmed event counter reset as indicated by a high signal on RSTCTRS line 99 or by programming of any event counter parameter with the exception of frame (expanded versus standard bin selection via FRZCONT line 212). During the reset sequence, the basic pattern is repeated 16 times. The pattern includes writing data from the RAM 240 onto the DATA bus 214, loading the data into the register, resetting the register, and writing back all 0's into the RAM. This sequence is performed beginning with RAM address 0000, and is repeated, with the address being incremented, until address 1111 of the RAM is written back to all 0's, at which point the reset sequence is complete. If an event counter reset is initiated during a trend analysis or histogram update sequence as described below, the reset sequence will take precedence, terminating the update sequence.

An uplink sequence is initiated by a programmed event counter uplink, as indicated by program/telemetry logic 90 (FIG. 1) by ACTEVT line 81 being set low. The uplink sequence uses the basic pattern a total of 17 times for each of two successive uplink transmissions. Starting with address 0000 of the RAM 240, data from that RAM address is loaded onto the 16-bit data bus 214, parallel loaded into the register 300, and serially written out onto the external telemetry bus 87, for transmission by telemetry logic 90. As the data is shifted onto EXTB bus 87, it is written back to the first bit of the register 290 so that the data written back into the RAM is the same as the data read from the RAM. The address is incremented and the pattern repeated until the data stored at address 1111 of RAM 240 has been written back. On using the basic pattern for the 17th time, data is enabled onto the data bus 214 from the memory cells 200 and sequence/control logic 260. This data is also parallel loaded into the register 300 and serially shifted onto the telemetry bus EXTB, but is not written back to the RAM. Upon finishing this basic pattern for the 17th time, the uplink sequence is complete. During the uplink sequence, histogram and trend analysis update sequences will not occur. If a trend analysis or histogram update sequence is triggered during an uplink sequence, it is acknowledged, but not processed, until the uplink sequence is complete.

A trend analysis update sequence is initiated each time CD line 228 from event counter 220 indicates that the number of events specified by TERM bus 204 have been counted. The type of events that are counted are determined by the data on SOURCE bus 202.

During each trend analysis update sequence, the basic pattern is used only once. Data is first enabled from address 0000 of the random access memory to the 16-bit DATA bus 214 and parallel loaded into the register 290. The 3-bits present on BIN bus 248, followed by the 2-bits present on PCT bus 232 are then serially shifted into the register, and the contents of the register are parallel loaded back to the random access memory. The RAM address is incremented after every third update, so that each address of the RAM contains the results of three sequential trend analysis updates (three 5-bit words). If the frame has been programmed to initial trend analysis, further updates will be blocked after the third update to the data stored in address 1111 of the RAM 240. If the frame has been programmed to final trend, the address will wrap around back to 0000, and trend analysis updates will continue. In this case, the random access memory will contain a record of the 48 most recent trend analysis updates.

Histogram update sequences are also initiated in response to a high logic level on CD line 228. The number of events counted is again determined by the information on TERM bus 204 and the events counted determined by the information on SOURCE bus 202. The basic pattern is used twice for each histogram update sequence, once to update the running count of average rate values and once to update the data regarding percent pace. The bin code on line 248 corresponds to the three most significant bits of the RAM address to be updated. The least significant address bit is 0 when updating the information stored regarding average rate, and 1 when updating the information regarding percent paced.

On initiation of the histogram update sequence, the number stored at the address specified by the bin code and 0 is read to the data bus 214 and parallel loaded into the register 290. One is added to the number in the register 290, and the new number is written back to RAM. The percent paced update immediately follows. The data in the address specified by the bin code and 1 is read onto the data bus 214 and parallel loaded into the register, incremented by the valve on the percent paced bus 232 1 and written back into the RAM. This completes the histogram update sequence.

During histogram update sequence, the most significant carry bit of each addition is checked. A carry in this position indicates that the data stored at that address in the RAM was all 1's prior to the addition step. At this point, the data in the register is not written back to the RAM, and a signal is generated on HISTDONE line 258 which blocks any further events from clocking the event and pace counters. No more histogram updates will be initiated, and the data present in the RAM at that point in time will not change until a reset sequence occurs.

The specific operations of the functional blocks are described in more detail below, in conjunction with FIGS. 3-7. The general operative scheme should be kept in mind when reviewing the following descriptions.

Figure 3A:
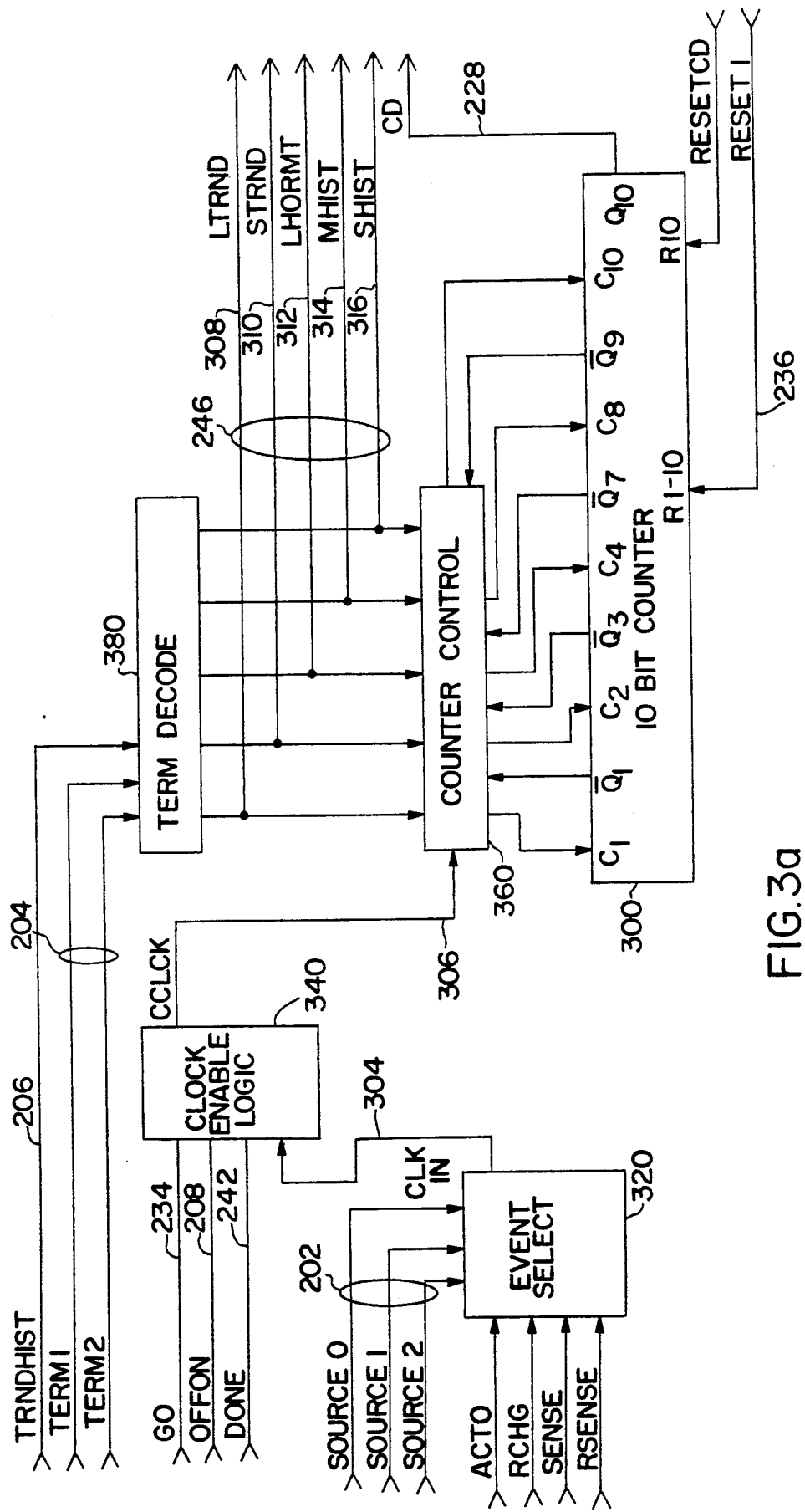
FIGS. 3A and 3B are schematic diagrams of the event counter circuitry illustrated in FIG. 2A.
Figure 3B:
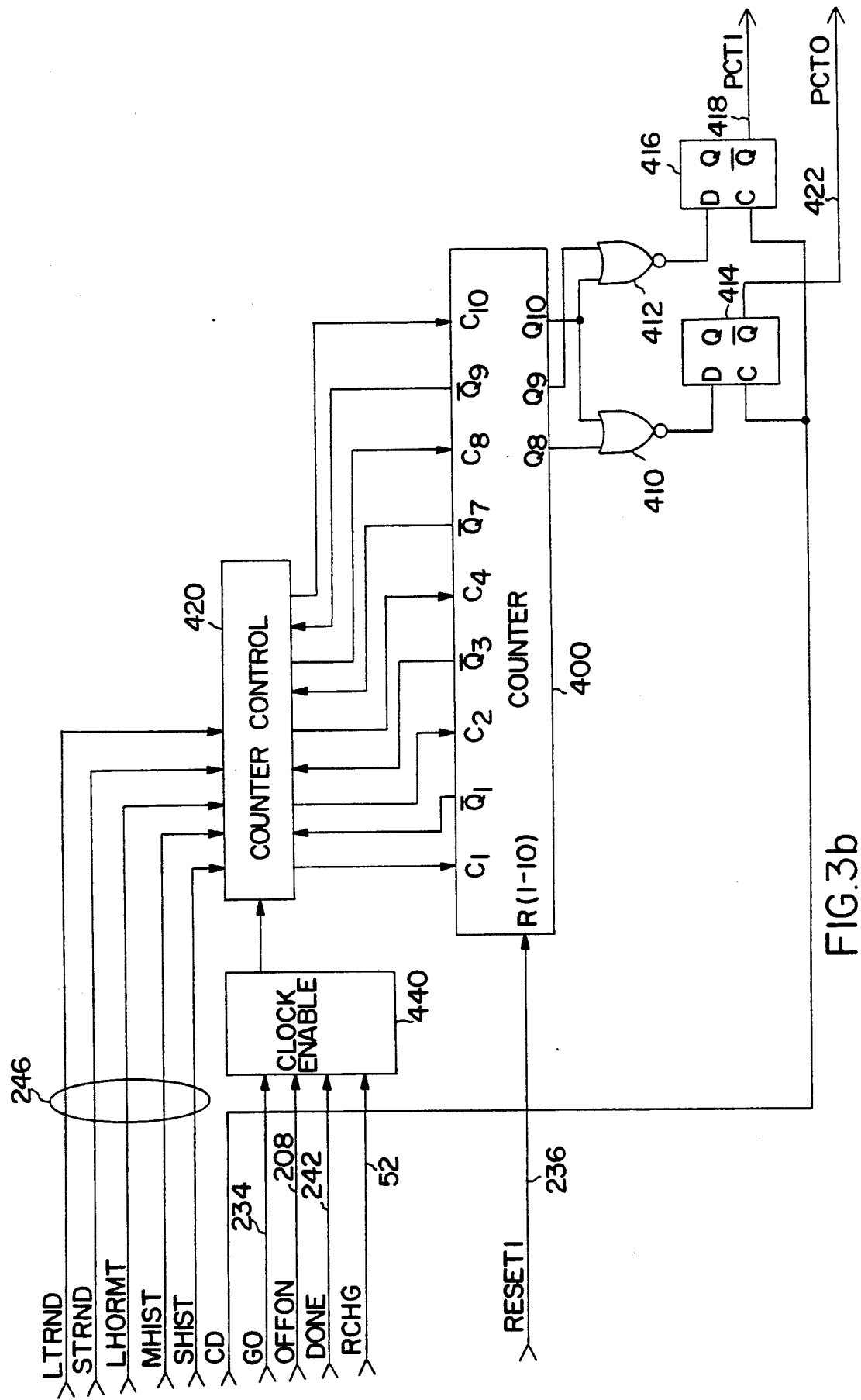

FIGS. 3A and 3B are functional diagrams of the circuitry in event counter block 220 (FIG. 2A). This functional block contains two counters, one for counting paced and sensed events (RCHG, SENSE, RSENSE, and ACTO signals), one for counting RCHG signals only. The first counter 300, referred to hereafter as the event counter, counts all events selected by event select logic 320. Event select logic is controlled by the information on the SOURCE bus 202 which selects among the ACTO, RCHG, SENSE, and RSENSE signals to determine which will pass through as clock signals on CLKIN line 304. Selection of counted events corresponds to chart 1, below.

CHART 1

| SOURCE2 | SOURCE1 | SOURCE0 | CLKIN |
|---|---|---|---|
| 0 | 0 | 0 | RCHG, SENSE |
| 0 | 0 | 1 | RCHG, SENSE, RESENSE |
| 0 | 1 | 0 | SENSE |
| 0 | 1 | 1 | SENSE, RSENSE |

CHART 1-continued

| SOURCE2 | SOURCE1 | SOURCE0 | CLKIN |
|---|---|---|---|
| 1 | 0 | 0 | ACTO |

Events to be counted, reflected by signals on CLKIN line 304 pass through clock enable logic 340, which is enabled by a high signal on GO line 234, and low signals on OFFON line 208 and DONE line 242. The detected events pass through on CCLK line 306, where they are applied through counter control logic 360 to clock counter 300. Counter control logic 360 determines the number of bits counted by counter 300 before CD line 228 goes high. This is accomplished by reconfiguring the counter, changing which is the least significant bit of the counter. For example, if the entire 10-bit counter chain is to be used, the clock signal on line 306 will be applied to the clock input of the first bit of the counter, and the not Q output of the first stage of the counter will be used to clock the second stage, etc. If, on the other hand, the second stage of the counter is selected, the clock signal on line 306 will be applied to the clock input of the second stage of the counter, and the not Q output of the first stage of the counter will be disabled from clocking the second stage. Using this basic format, counter control logic 360 may select either the first, second, fourth, eighth or tenth stage of the counter as the least significant bit. If the tenth stage of the counter is selected, of course, only a single event is counted. Selection of the number of events counted is accomplished by term decode logic 380, under control of the information on TRNDHST line 206 and on TERM bus 204. The outputs of term decode logic 380 appear on 5-bit bus 246. Only one of the five lines of bus 246 is set high at any one time. LTRND line 308 is set high if long term trend analysis is selected, and corresponds to a count of 512 events. STRND line 310 is high if short term trend analysis has been selected, and corresponds to a count of 64 events. LHORMT line 312 is set high if long term histogram or short term trend analysis has been selected, and corresponds to a count of 256 events. MHIST line 314 is set high if medium term histogram storage has been selected, and corresponds a count of four events. SHIST line 316 is set high if the short term histogram storage has been selected, and corresponds to a count of 1 event.

The number of events counted for each average rate calculation determines the overall time period represented by the data stored in the random access memory for the trend analysis and histogram storage functions. If short term trend analysis is elected, the random access memory will store information reflecting approximately ⅔ of one hour. If medium term trend analysis is selected, the random access memory will store data reflective of approximately three hours. If long term trend analysis is selected, random access memory will hold data reflective of approximately 6 hours. If short term histogram analysis is selected, random access memory will hold data indicative of approximately five hours. If medium term histogram analysis is selected, random access memory will hold data indicative of approximately 21 hours. If long term histogram analysis is selected, random access memory will hold data indicative of approximately six months.

The values on 5-bit bus 246 are also used to control a second counter 400, referred to as the percent paced counter. This counter, like the event counter 300, is a 10-bit counter which may have its least significant counting bit selected from between its first counting stage, second counting stage, fourth counting stage, eighth counting stage and tenth counting stage by means of counter control logic 420. Percent paced counter 400, like event counter 300, is reset by RESET1 line 236. Signals on RCHG line 52 are passed through clock enable logic 440 to counter control logic 420. Under control of counter control logic 420, they are passed through to clock the selected least significant bit of counter 400. Clock enable circuitry 440, like clock enable logic 340 (FIG. 3A), is enabled by means of a high signal on GO line 234 and low logic levels on OFFON line 208 and DONE line 242. The Q outputs of the last three stages of counter 400 are used to derive an indication of the number of pacing pulses counted while counter 300 (FIG. 3A) is counting. The Q outputs of the last three stages of counter 400 are passed through NORGATES 410 and 412, which serve as data inputs to latches 414 and 416. These latches are clocked by a high signal on CD line 228 from event counter 300, indicating that the predetermined number of desired events has been counted.

The data on PCT0 line 420 and PCT 1 line 418 reflect a percentage of counted events which corresponded to cardiac pacing pulses, indicated by signals on RCHG line 52. The correspondence between this information and the percentage paced is set forth in Chart 2 below.

CHART 2

| PCT1 | PCT0 | PERCENT PACED RANGE |
|---|---|---|
| 0 | 0 | 0 <= pct paced < 25% |
| 0 | 1 | 25% <= pct paced < 50% |
| 1 | 0 | 50% <= pct paced < 75% |
| 1 | 1 | 75% <= pct paced <= 100% |

Figure 4A:
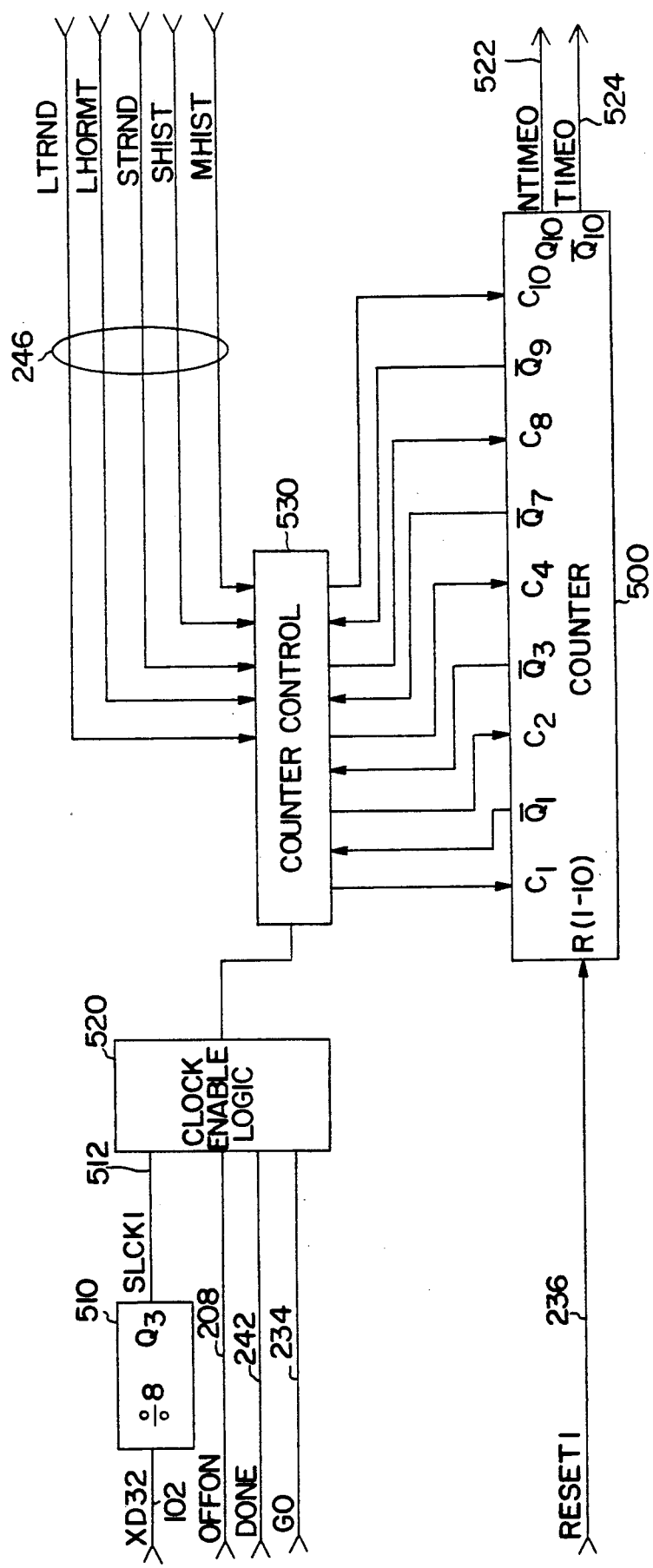
FIGS. 4A and 4B are schematic diagrams of the timer circuitry illustrated in FIG. 2B.
Figure 4B:
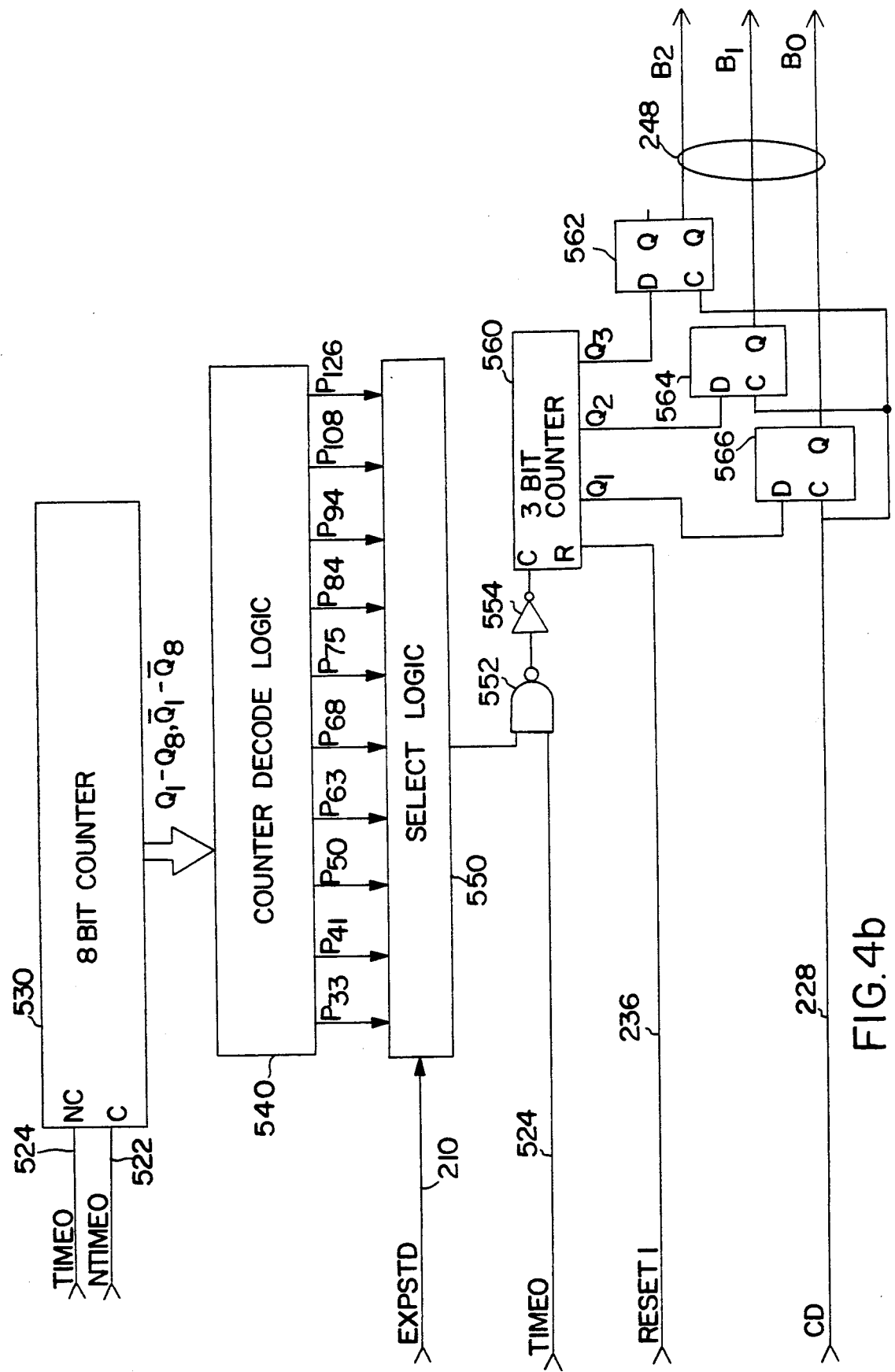

FIGS. 4A and 4B are functional diagrams of the timer logic 280, illustrated in FIG. 2B. The purpose of this logic is to determine the bin code present on BIN bus 248 for each histogram and trend analysis update sequence. Timer block 280 keeps track of the amount of time it takes for the number of events specified by the data on TERM bus 204 to be counted in order to determine an average rate value which falls into one of eight rate ranges. This is accomplished by means of a 10-bit counter 500 which, like the counters in event counter logic 220, is reset by a signal on RESET1 line 236, concurrent with the event counter 300 and percent paced counter 400. The clock signal for the counter is applied via XD32 line 104 which is further divided by eight by means of a 3-bit counter 510, passed through clock enable logic 520 and applied to counter control logic 530. Clock enable logic 520 will pass the clock signal on SLK1 line 512 through to counter control logic 530 in the presence of a high signal on GO line 234 and low signals on OFFON line 208 and DONE line 242. Counter control 530 is controlled by the 5-bit bus 246 in the same fashion as counter control 420 associated with percent paced counter 400 (FIG. 3B). At overflow of the counter, NTIMEO line 522 goes high and TIMEO line 524 goes low. These signals are used to clock a second 8-bit counter 530. The Q and not Q outputs of counter 530 are applied to counter decode logic 540, which generates high signals on lines P33, P41, P43, P50, P63, P68, P75, P84, P94, P100 and P126 during corresponding counts of 8-bit counter 530. Select logic 550 selects between the outputs of counter decode logic 540 and passes selected ones of said outputs out via NAND gate 552, inverted by inverter 554 to act as clock signals for 3-bit counter 560. If the standard rate bins have been elected as signified by a low signal on EXPSTD line 210, select logic passes clock signals through to 3-bit counter 560 on counts 63, 68, 75, 84, 94, 108 and 126. If EXPSTD line 210 is high, counts are passed through to clock 5-bit counter 560 on counts 33, 41, 50, 63, 75, 94 and 126.

3-bit counter 560 serves to provide the decoded average pacing rate, expressed in terms of a bin code on BIN bus 248. Counter 560 is reset by a reset signal on RESET1 line 236. Its Q outputs are passed through to latches 562, 564 and 566, which are clocked by CD line 228. The values on the three lines of BIN bus 248 reflect which of the eight available rate ranges the average event rate falls into. Correspondence between the bin codes on BIN bus 248 and average event rates is set forth in Chart 3 below.

CHART 3

| RATE RANGE (bpm) | EXPSTD | B2 | B1 | B0 |
|---|---|---|---|---|
| >120 | 0 | 0 | 0 | 0 |
| >110–120 | 0 | 0 | 0 | 1 |
| >100–110 | 0 | 0 | 1 | 0 |
| >90–100 | 0 | 0 | 1 | 1 |
| >80–90 | 0 | 1 | 0 | 0 |
| >70–80 | 0 | 1 | 0 | 1 |
| >60–70 | 0 | 1 | 1 | 0 |
| <=60 | 0 | 1 | 1 | 1 |
| >220 | 1 | 0 | 0 | 0 |
| >180–220 | 1 | 0 | 0 | 1 |
| >150–180 | 1 | 0 | 1 | 0 |
| >120–150 | 1 | 0 | 1 | 1 |
| >100–120 | 1 | 1 | 0 | 0 |
| >80–100 | 1 | 1 | 0 | 1 |
| >60–80 | 1 | 1 | 1 | 0 |
| <=60 | 1 | 1 | 1 | 1 |

As noted above, the values on BIN bus 248 are stored in the random access memory during trend analysis and are used to address the random access memory during histogram storage.

Figure 5A:
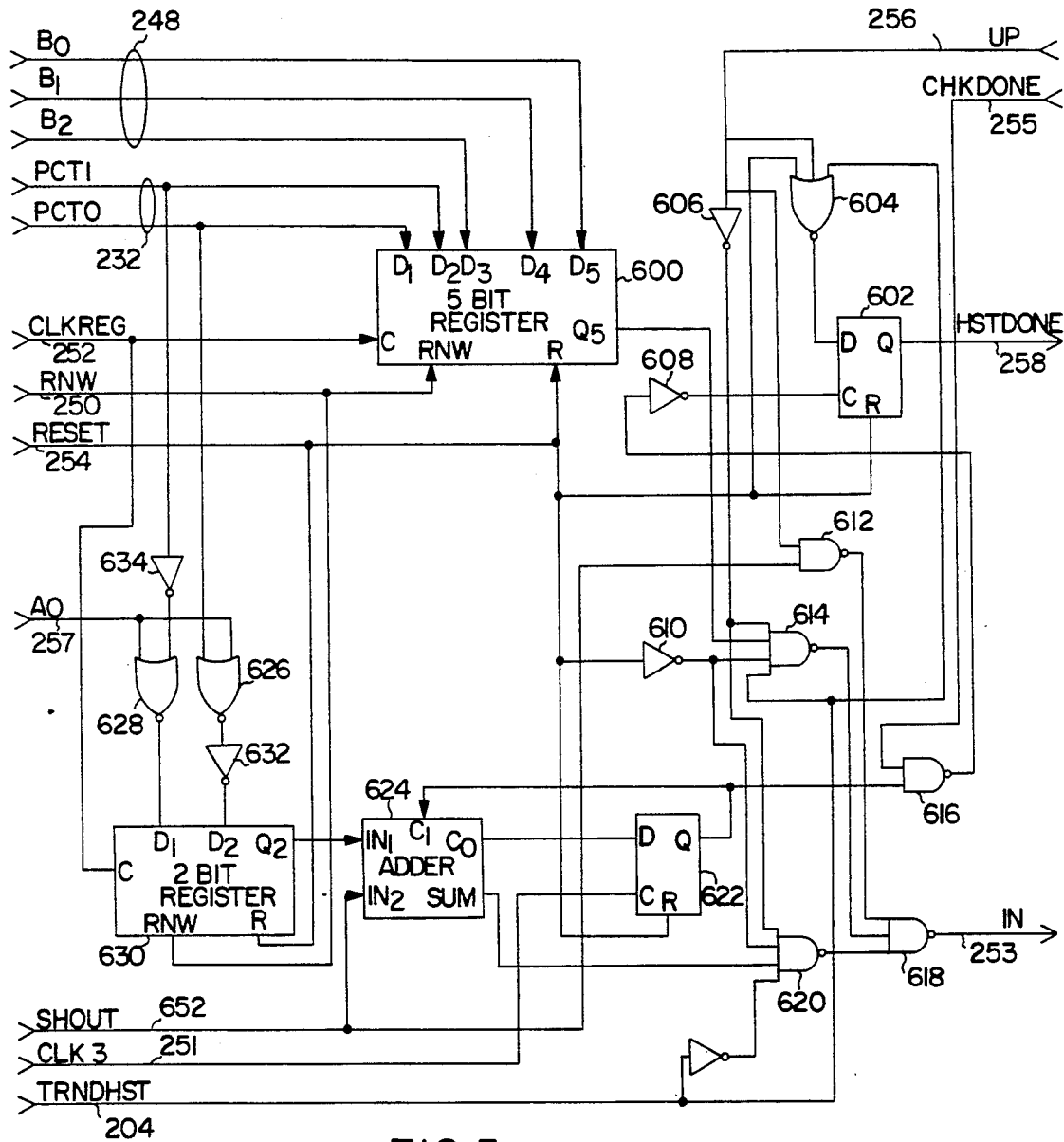
FIGS. 5A and 5B are schematic diagrams of the register circuitry illustrated in FIG. 2B.
Figure 5B:
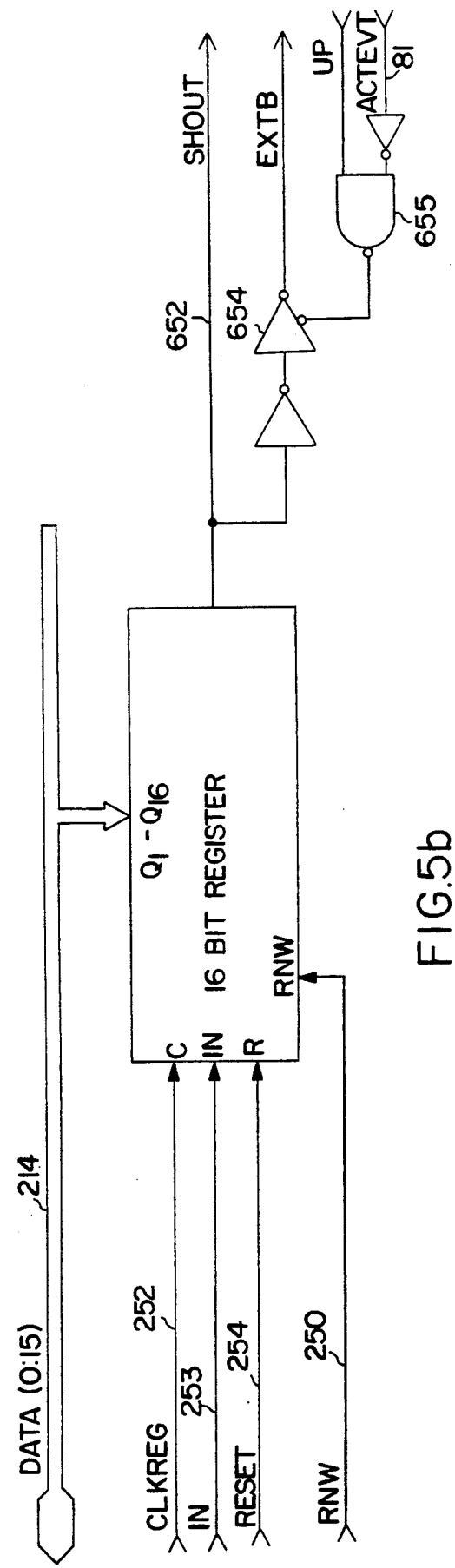

FIGS. 5A and 5B are a functional schematic of the register logic 290 illustrated in FIG. 2B. The function of the circuitry illustrated in FIGS. 5A and 5B is to operate on data after being read from the RAM 240 and before being written back into the RAM. As discussed, data is read from the RAM onto the DATA bus 214, parallel loaded into the register, shifted and written back to the RAM.

Figure 6A:
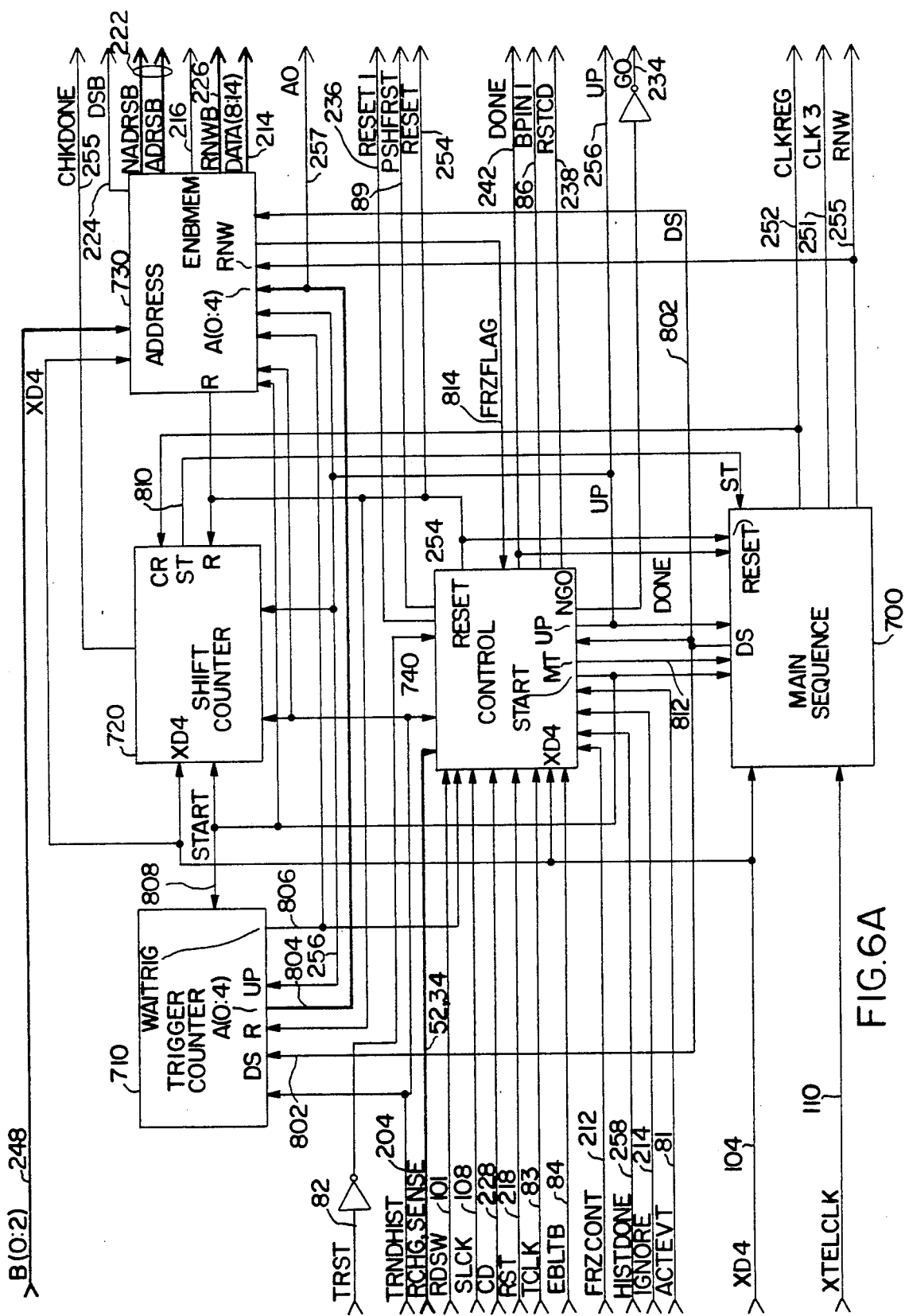

16-bit register 650 (FIG. 5B) serves as the actual shift register portion of the register block. The data bus 214 provides a parallel input and output to the register 650, with parallel input being enabled when RNW line 250 is high. RNW 250 is controlled by sequence control logic 260 (FIG. 6A). Clocking of the shift register 650 is accomplished by clock signals present on CLKREG line 252 from sequence control logic 260. IN line 253 serves as the serial input, and SHOUT line 652 serves as the serial output from the register. During telemetry, when ACTEVT line 81 is low and the UP 256 line is high, inverter 654 is enabled to pass the serial output of shift register 650 through to the external telemetry bus (EXTB) 87 for transmission out of the pacemaker by program/telemetry logic 90 (FIG. 1).

Register 600 (FIG. 5A) receives parallel data input from BIN bus 248 and PCT bus 232, and provides a serial output of its contents on line 654. Like register 650, it is clocked by clock signals on CLKREG line 252 and reset via RESET line 254, both from sequence/control logic 260.

During the trend analysis update sequence, after placing of the information stored at the then currently selected address of RAM 240 onto data bus 214, on the next rising edge clock signal on CLKREG line 252, while RNW line 250 is high the values on the BIN bus 248 and PCTO 232 are parallel loaded into shift register 600, while the values on DATA bus 214 are parallel loaded into 16-bit shift register 650. RNW line 250 is then set low and data stored in 5-bit register 600 is serially shifted through NANDGATE 614 and NAND gate 618 to IN line 253 of shift register 650 by five CLKREG pulses on CLKREG line 252. The contents of shift register 650 are then written back onto the data bus 214 and into the random access memory on the next data strobe signal on DSB line 224 from sequence/control logic 260. Thus, each trend analysis update adds 5-bits of data to the random access memory. The address of the random access memory being updated is incremented by one, after each three trend analysis update sequences.

During the histogram update sequence, the data located at the RAM address corresponding to the bin code and O is loaded onto data bus 214, and is parallel loaded into 16-bit shift register 650 on the leading edge of the next clock signal on CLKREG line 252 while RNW line 250 is high. AO line 257 is set high by sequence control logic 260, so that (0,1) is written into 2-bit shift register 630 by the same register clock pulse. The output of 2-bit register 630 is presented to the input of a 1-bit full carry adder circuit 624. On the next 16 rising edges of the CLKREG signal, 16 1 bit additions are performed, with the result of those additions being passed through NAND gate 620 and NAND gate 618 to IN line 253, where they are shifted back into 16-bit shift register 650. The carry output of adder 624 is clocked into flip-flop 622 by a clock signal on CLK3 line 251. The net result is that the original word stored in 16-bit register 650 is written back to the register, incremented by one.

After the 16th shift of register 650, CHKDONE line 255 is set high by sequence control logic 260. The carry output of adder 624, previously latched into flip-flop 622 is checked. If the carry output of adder 624 is high, flip-flop 602 will be clocked via NAND gate 616 and inverter 608 to set HISTDONE line 258 high, which will cause the sequence control block 260 to set DONE line 242 high which, as discussed above, terminates operation of the event counters and also blocks further data from being written back to the RAM. Reset of the register block is accomplished via RESET line 254, which also resets flip-flops 602 and 622, as well as disabling passage of signals through NAND gates 620, 618 and nor gate 604, while the reset line is held high.

This new word is then written back to the RAM via data bus 214. On the next clock signal on CLKREG line 252, the information on bus 232 is loaded into two bit register 630, AO line 253 having previously been set low. Simultaneously, the data stored at the RAM address corresponding to the bin code and 1 is loaded into 16-bit shift register 650. In response to the next 16 clock signals on CLKREG line 252, have the effect of adding the percent paced code (0, 1, 2 or 3) to the value initially stored in the RAM. This new value is then written back into the RAM via DATA bus 214.

Because the value stored at the address corresponding to the bin code and 1 is incremented by the percent paced code, rather than simply incremented by 1, the value stored therein is a weighted count, which may be compared to the count stored in the address corresponding to the same bin code and 0 to determine a cumulative percent paced value. For example, in a patient who was paced 100% of the time, the values stored in the address corresponding to the bin code and 1 would be three times the value stored in the address corresponding to the bin code and 0. This relationship allows an external monitoring device receiving the telemetered values stored at these addresses to decode the measurement of the cumulative percent paced, within the rate range corresponding to the bin code.

The external monitoring device may easily determine the cumulative percentage paced by dividing the value stored in the address corresponding to the bin code and 1 (percent paced bin) by the value stored in the value corresponding to the bin code and 0 (events bin). The value displayed for cumulative percentage paced may vary continuously as a function of this quotient, or may itself be divided into distinct percentage paced ranges, such as 0–25 percent (corresponding to a quotient of $0-<0.5$), 25–50 percent (corresponding to a quotient of $0.5-<1.5$), 50–75 percent (corresponding to a quotient of $1.5-<2.5$), and 75–100 percent (corresponding to a quotient of $>=2.5$.

During uplink sequence, as indicated by a high logic level on UP line 256, NAND gates 614 and 620 are disabled, while NAND gate 612 is enabled to pass the serial output of shift register 650 through to IN line 253 via NAND gate 618. As a result, during the uplink sequence, data is parallel loaded from data bus 214 into 16-bit register 650, sequentially shifted 16 times to SHOUT line 652 and thereby to the external telemetry bus, while simultaneously being shifted back into the 16-bit register 650 on IN line 253. After 16 shifts, the data is written back into the random access memory.

Operation of the register 650 during a reset sequence does not involve any shifting of the register, but instead, as described above, merely involves sequential loading of data from the random access memory into the shift register, resetting of the shift register to 0 via reset line 254 and returning the contents of the shift register 650, now all 0's, to the random access memory.

FIGS. 6A, B, C and D illustrate the sequence control logic block 260 illustrated in FIG. 2. These figures should be considered together. FIG. 6A shows the functional organization of the sequence control block and the interconnects between the trigger counter, shift counter, address, control and main sequence blocks. The trigger counter, shift counter and address blocks are described in more detail in FIG. 6B, 6C and 6D, respectively.

FIG. 6A shows the interconnection of the functional blocks within the sequence control logic and their connection to the remainder of the event counter logic. Signal lines corresponding to those illustrated in previous drawings are labeled identically in FIG. 6A.

Trigger counter logic 710, illustrated in more detail in FIG. 6B is a 6-bit counter clocked by the data strobe signal on DS line 802 provided each time data is read into or out of random access memory 240. Thus, 6-bit counter 820 counts the number of data strobes that occur. The not Q outputs of counter 820 are available on A bus 804. Counter 820 is reset in response to a positive pulse on START line 808, from control logic 740, via flip-flop 822, NOR gate 824 and inverter 826. The Q2, Q3 and Q6 outputs of counter 820 are passed through counter decode logic 828, which is controlled by TRNDHST line 204, RESET line 254, and UP line 256. If RESET line 254 is low and UP line 256 is high, indicating that an uplink sequence is taking place, counter 820 counts 34 clock cycles before WAITRIG line 808 becomes true. Because there are two data strobes per each basic pattern (transfer of data from RAM 240 to register 290 and back) this represents 17 repetitions of the basic pattern, reflecting telemetry of the contents of all 16 addresses in the random access memory followed by telemetry of the 9-bits stored in the memory cells, and of information from sequence/control logic 260, as discussed above. If RESET line 254 is set high and UP line is set low, indicating a reset sequence, WAITRIG line 808 goes high after 32 data strobes on line 802 indicating 16 repetitions of the basic pattern, reflecting resetting to 0 of all 16 addresses in the RAM 240. If TRNDHST line 204, RESET line 254 and UP line 256 are all set low, indicating a histogram storage update, WAITRIG line 808 goes high after four clock cycles, indicating two repetitions of the basic pattern, reflecting updating of the random access memory corresponding to the bin code on BIN bus 248 plus 0 and corresponding to the bin code plus one. If TRNDHST line 204 is high and RESET line 254 and UP line 256 are low, indicating trend analysis, WAITRIG line 808 goes high after two data strobes, reflecting one repetition of the basic pattern occurring during the trend analysis update.

The shift counter circuitry illustrated in FIG. 6C counts shifts of the shift register 650 (FIG. 5B) in register logic 290. The shift counter circuitry 720 includes a 5-bit counter 840, which is reset by a signal on START line 808, via NOR gate 842 and inverter 844. Counter 840 is clocked by clock signals on CLKREG line 252, and the Q1, Q2, Q3 and Q5 outputs of the counter are applied to counter decode logic 846. Counter decode logic 846 is controlled by TRINDHST line 204, UP line 256 and RESET line 254, analogous to counter decode 828 associated with the trigger counter. During reset sequences, counter decode 846 applies a positive logic level on ST line 810 after one count, indicating that only one clock pulse is applied to the register logic, the pulse used to parallel load the data into shift register 650 (FIG. 5B). If an uplink sequence is in effect, 17 clock register cycles are counted before ST line 810 goes high, signifying the initial clock cycle which loads the information on data bus 214 into shift register 650, followed by the 16 clock cycles during which data is serially shifted out of shift register 650 on to the external telemetry bus. Similarly, if a histogram update sequence is in effect, ST line 810 also goes high after 17 shift register clock cycles on line 252, indicating the initial loading of the data from the data bus into the shift register followed by the 16 shifts and 1-bit additions performed during the update of the value stored at one address in the RAM 240. If a trend analysis update is in effect, ST line 810 goes high after 6 shifts, reflecting the initial loading of the 5-bits from the bin bus 248 and the PCT bus 232 into the 5-bit shift register 600, followed by the five register clock cycles on line 252 which clock the 5-bits in shift register 600 into shift register 650. If a histogram update sequence is in effect, CHKDONE line 255 also goes high after 17 register clock cycles on line 252, triggering the checking of the carry output of the addition to the most significant bit of the shift register, as discussed above in conjunction with the description of the register logic 290.

FIG. 6D illustrates the address circuitry 730, which controls which of a number of sources are used to generate the addressing scheme employed during the reset, uplink, trend analysis update and histogram update sequences. Selection is made by address select block 900, under control of RESET line 254, TRNDHST line 204 and UP line 256. During reset sequences, the addressing scheme is generated by the Q outputs of the trigger counter 820, applied to the address select logic 900 via A bus 804. Address select logic 900 passes the selected addresses through to buffer inverters 902 to generate buffered positive and negative address signals on bus 222.

The addressing scheme for trend analysis operation employs 6-bit counter 910, which is reset by a reset signal on RESET line 254, and is clocked by WAITRIG line 808 through NOR gate 904, enabled by a low signal on UP line 256. The Q outputs of the third, fourth, fifth and sixth stages of 6-bit counter 910 are applied to address select logic, and define the RAM address during trend analysis operation. The Q outputs of the two first stages of counter 910 are applied to NAND gate 908, to generate a clock signal for the remainder of the counter every third signal on WAITRIG line 808. Thus, the RAM address is incremented every third trend analysis update, as discussed above. PTR1 line 912 and PTR2 line 914 function as a pointer, indicative of which of the three available 5-bit spaces within each individual RAM address are presently being written to. In response to a count of all 1's in the final four stages of counter 910, FRZFLAG line 814 is set high. FRZFLAG line 814 is provided to control logic 740 (FIG. 6A) and is used to disable further operation of the trend analysis function after the third update of RAM address 1111 if FRZCONT line 212 is set high indicating selection of the initial trend frame.

The addressing scheme for the uplink sequence employs the data on A bus 804. Bits 0-3 act as an address in the same way as during the reset sequence, beginning with address 0000 and incrementing after each basic pattern until address 1111 has been operated on. After address 1111, bit 4 on bus 804 is used to enable the last 16 bits of uplink information onto DATA bus 214 by activating ENBMEM line 216, which enables parallel transfer of the 9 bits stored in the memory cells 200, the present address from 6-bit counter 910, the pointer bits on PTR1 line 912 and PTR0 line 914 and the logic state of the Q output of flip-flop 913 on FRZFLAG line 814 to be parallel loaded onto DATA bus 214, where they are shifted through the shift register 650 (FIG. 5B) and onto the external telemetry bus. In addition, in response to bit 4 on A bus 804 going high, address select logic 900 sets BLOCK line 916 high, preventing passage of the data strobe signal on DS line 802 through to DSB line 224. This prevents any reading to or writing from the random access memory during transmission of the final 16-bits of telemetry.

Transmission of the information on PTR1 line 912 and PTR0 line 914 in conjunction with transmission of the present address derived from 6-bit counter 910 is necessary in conjunction with the trend analysis function. As noted above, during uplink sequence, value stored in the random access memory are telemetered out in sequential order beginning with address 0000 and ending with address 1111. Transmission of the pointer bits (PTR1, PTR0) in conjunction with the address indicates the next available storage and allows an external monitoring device to determine which of the stored values in the random access memory is the most recent. This facilitates allowing display of the stored values in correct time order, ending with the value stored at storage space immediately preceding that indicated by the address and pointer location indicated by telemetry.

During a histogram update sequence, information on BIN bus 248, in conjunction with the data strobe signal on line 802 is used to provide the addressing scheme. The information on data bus 248 provides the first three bits of the address, while the data strobe signal on DS line 802, divided by 4 by 2 bit counter 918 provides the fourth bit. Thus, during the first two data strobe signals during a histogram update sequence, the fourth bit of the address will be 0. During the second two data strobes, the fourth bit of the address will be 1. As discussed above, four data strobe signals (2 basic patterns) occur during a single histogram update sequence, providing for updating of the information stored at two sequential addresses in the random access memory 240.

The function of the control block 740 (FIG. 6A) is to acknowledge triggers for each sequence, give a starting point for data collection on GO line 234 and generates a signal to block further data collection on DONE line 242.

As discussed above, a reset sequence is triggered by event counter logic programming (except frame) and by event counter reset via telemetry/programming logic 90. In response to a positive going signal on RST line 218, indicating the initiation of a reset sequence, control logic 740 sets RESET line 254 high. Following this START line 808 is set high, which initiates the sequence control logic MT line 812 is then set high triggering the first data strobe by main sequence logic 700 on DS line 802. Main sequence logic 700 then passes register clock pulses through to register logic 290 until ST line from shift counter 720 810 goes high. This triggers the second data strobe of the basic pattern, This pattern is repeated until WAITRIG line 806 goes high, indicating the end of the reset sequence.

The uplink sequence is initiated upon programming of an event counter uplink code into program/telemetry logic 90 (FIG. 1). In response to decoding a request for event counter uplink, program/telemetry logic 90 sets ACTEVT line low, which will delay any trend analysis or histogram update trigger until after the uplink sequence is complete. Program/telemetry logic 90 also sets EBLTB line 84 high during uplink telemetry. EBLTB line 84 is buffered by control logic 740 to produce UP line 256 indicating that an uplink sequence is occurring. On the next XD4 clock cycle after UP line 256 is set high, START line 808 is set high to reset the sequence control logic to a known state and MT line 812 is used to trigger the initial data strobes of the basic pattern with ST line 810 triggering the second strobe as above. This pattern is repeated until WAITRIG line 808 goes high indicating the end of the first telemetry transmission. This process is repeated a second time, and after the second telemetry transmission, control logic 740 sets PSHFRST line 89 high, resetting the shift register in program telemetry logic 90, ending the uplink sequence, allowing EBLTB line to go low and ACTEVT line to go high. At this time, any trend analysis or histogram update triggers that occurred during the uplink will be processed.

Control logic 740 initiates a trend analysis or histogram update sequence in response to a positive going signal on CD line 228, resulting in RSTCD line 238 being set high to reset the final stage of the event counter 220. Assuming that neither the reset sequence nor the uplink sequence are in progress (RESET line 254 and UP line 256 low) a positive signal on START line 808 will reset the sequence control circuitry in its entirety, with the basic pattern repeating as above until WAITRIG line 808 goes high.

When the event counter logic has been programmed to count only SENSE and RSENSE signals, IGNORE line 244 is high during each RCHG signal on line 52. In response to a high signal on IGNORE line 244, control logic 740 generates a new start signal on line 808.

The function of main sequence block 700 is to generate the fundamental signals which define the basic pattern. At the onset of each sequence, the start signal resets the main sequence block. In response to the receipt of signals on MT line 812, main sequence logic 700 provides data strobe signals on DS line 802 which, in conjunction with the read not write signal (RNW) on line 255, are used to control writing to and reading from the random access memory 240. Two data strobe signals are generated during each basic pattern. During the first data strobe, read not write line 255 is high enabling transmission of the data in the RAM to the data bus. During the second data strobe, read not write line 255 is low, enabling writing of data on the data bus 214 back into the random access memory.

In addition, main sequence logic 700 provides the register clock signal (CLKREG) on line 252 which clocks the shift register logic 290. During any basic pattern, the initial clock register signal accomplishes parallel loading of the data on the data bus 214 into register 650 in response to a clock cycle while read RNW line 255 is high. Subsequent register clock cycles serve to shift the register 650 (as described above). Main sequence logic 700 uses the clock signals on XD4 line 104 for all sequences other than uplink and uses the telemetry clock signal on XTELCLK line 110, from program/telemetry logic 90 to provide shifting of the register 650 for the uplink sequence.

After the appropriate number of register shifts have been performed, the shift counter block 720 will generate an ST signal, as discussed above, which will block further clock register signals.

As noted above, upon detecting that the most significant carry from the shift register is a logic 1 during a histogram update sequence, the high signal on DONE line 242 blocks the second data strobe of the basic pattern in progress. A high signal on RESET line 254 or a high signal on UP line 256 will enable the final data strobe, allowing the word stored in the register 650 to be enabled for reset or telemetry transmission during an uplink sequence.

Figure 7:
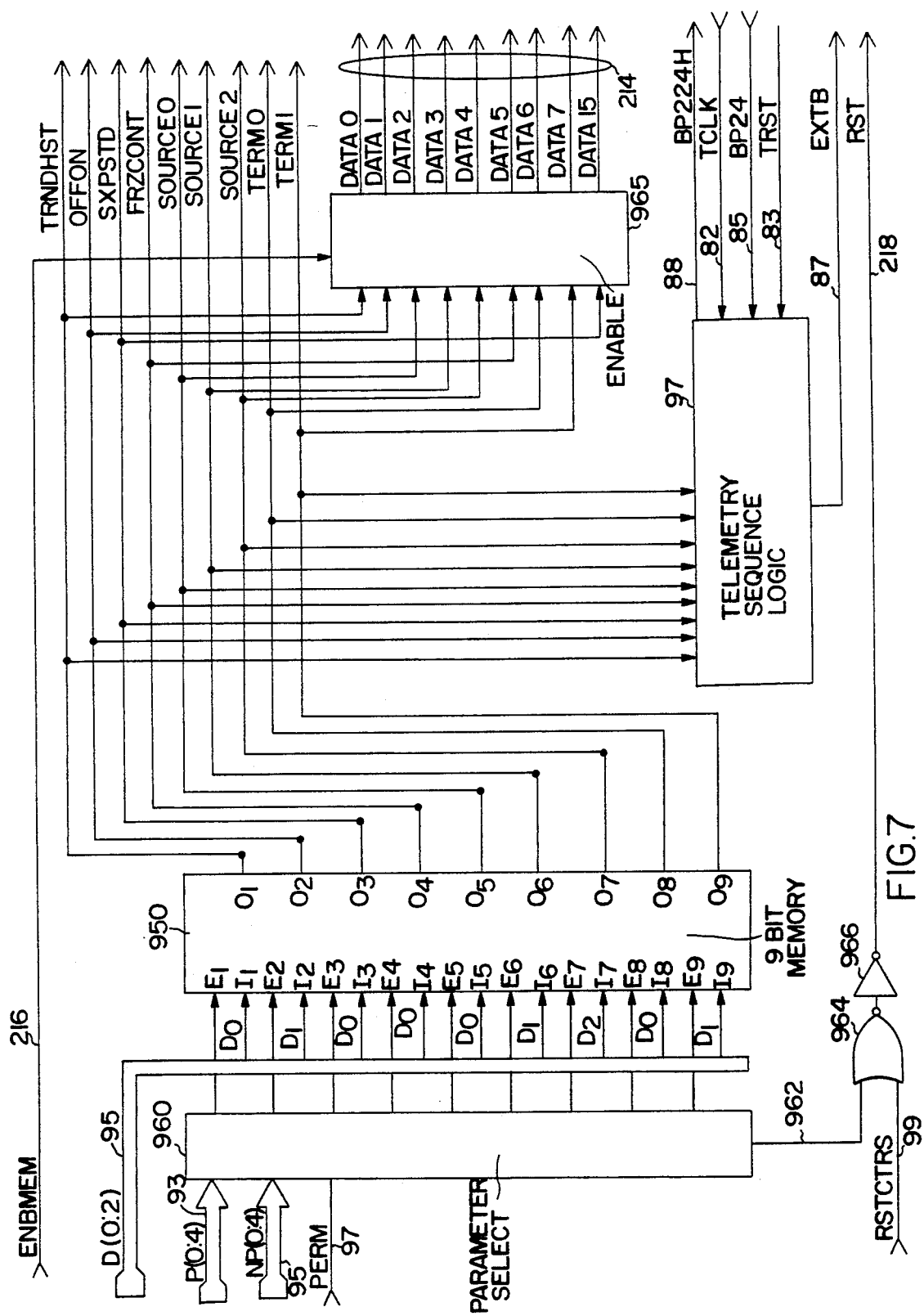
FIG. 7 illustrates the memory cell circuitry illustrated in FIG. 2A.

Memory cells 200 are illustrated in FIG. 7. Memory cell logic 200 includes a 9-bit memory 950 which has nine memory stages each with a data input (I), a write enable input (E), and a data output (O). Data to be loaded into the memory is available on the 3-bit D bus 95 from program/telemetry logic 90. Selection of the particular stages into which the information on D bus 95 is to be loaded is determined by the parameter select logic 960 in response to the parameter codes on P bus 93 and NP bus 95, from program/telemetry logic 90. Programming of 9-bit memory 950 is enabled while PERM line 97 is high. In addition, parameter select logic 960, in response to the reprogramming of any parameter other than frame (initial trend versus final trend) generates a reset signal on line 962. NOR gate 964 and inverter 966 sets RST line 218 high, resetting the event counting circuitry as described above. A high signal on RSTCTRS line 99, indicating a request for event counter reset from program/telemetry logic 90 will also cause a reset signal to be generated on RST line 218. In addition to the designated output lines IRNDHIST line 206, OFFON line 208, etc.), the data stored in the 9-bit memory is also available to lines 0-7 and 15 of data bus 214, in response to a low signal on ENBMEM line 216, produced by the address logic 730 (FIG. 6A), so that it may be parallel loaded into shift register 650 (FIG. 5B) and serially shifted onto the external telemetry bus 87 by 16-bit register 650.

In addition, the contents of the memory 950 are available in serial format to the external telemetry bus 87 by means of telemetry sequence logic 970, activated during a telemetry transmission of programmed parameters stored in program/telemetry block 90. Telemetry sequence logic 970 is reset via TRST line 83 and initiated by a signal on BP24 line 85. Under control of the clock signals on TCLK line 82, the data stored in 9-bit memory 950 is sequentially applied, one bit at a time, to external telemetry bus 87. After the ninth bit has been applied to the telemetry bus, telemetry sequence logic 970 sets BP24H line 88 high, indicating that the entire contents of the memory have been provided.

Figure 8C:
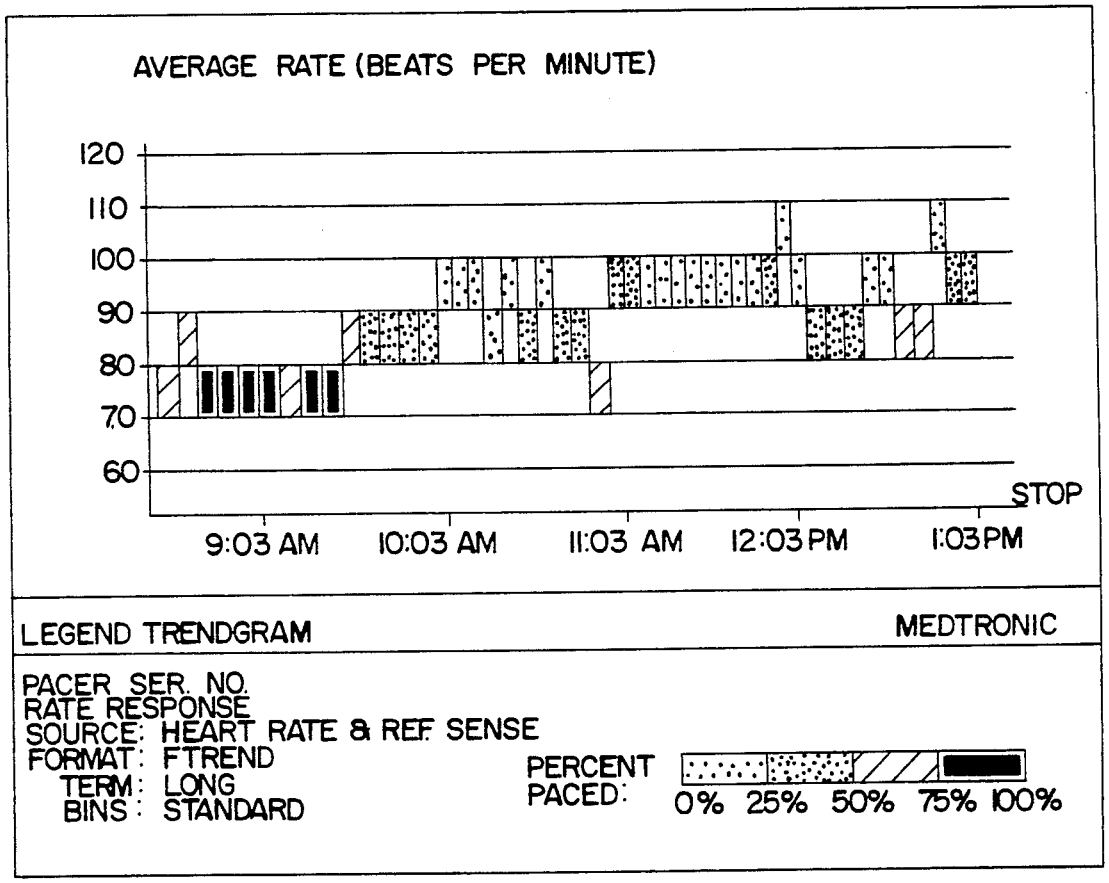
Figure 8D:
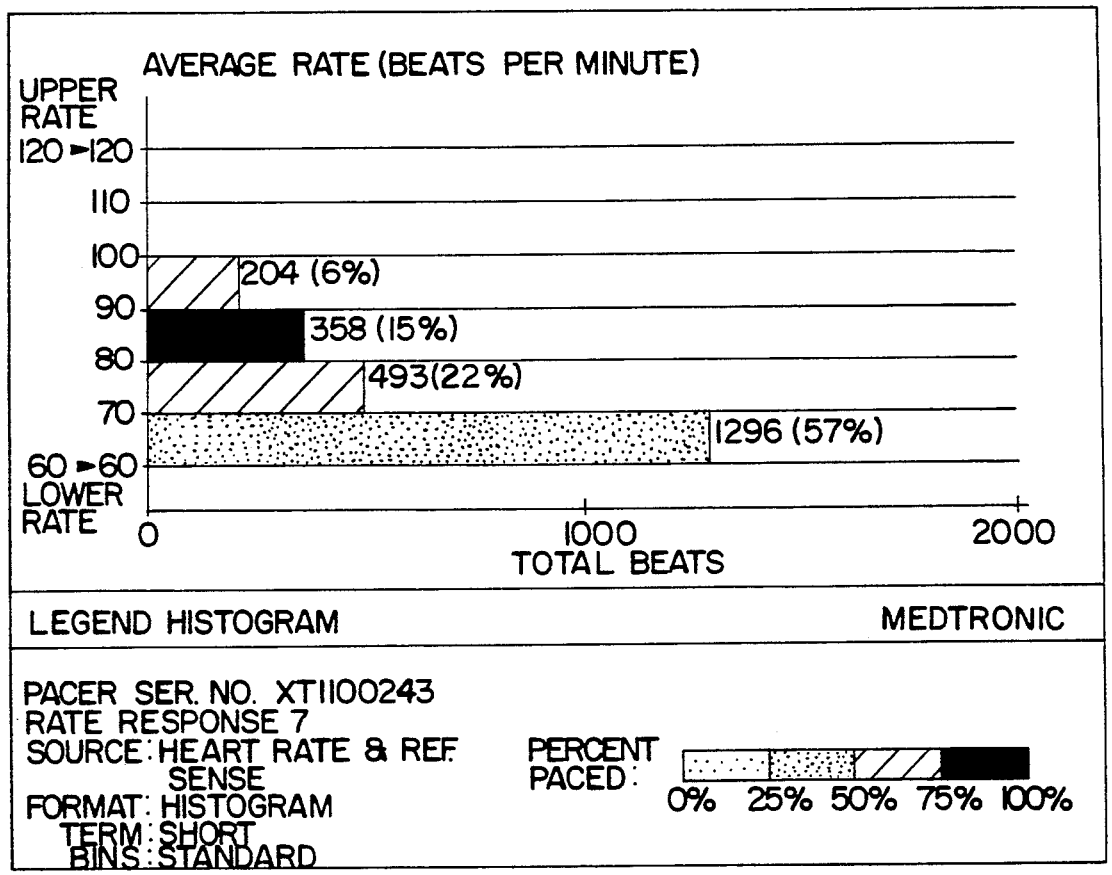

FIGS. 8A, 8B, 8C and 8D illustrate suitable display formats for the information stored in the event counter circuitry discussed above. Information stored by the event counter circuitry and made available to an external monitoring device by means of the programming-/telemetry logic provides sufficient information to generate any of the displays illustrated. FIGS. 8A and 8B are simple listings of the information stored by the event counter in histogram and trend analysis modes. FIGS. 8C and 8D are graphic depictions of information stored during histogram and trend analysis operation.

FIG. 8A shows a typical display of the information stored in the event counter circuitry during trend analysis. Information is displayed in three columns entitled "Elapsed Time", "Average Rate" and "% Paced", all of which are readily derived from the information telemetered out of the pacemaker by the program/-telemetry logic 90. The values illustrated in the average rate column simply correspond to the sequential bin codes store in the random access memory, with average rate displayed equal to a rate in the middle of the rate range corresponding to the stored bin code. Correspondence between rate ranges and bin code is decoded according to the numbers illustrated in Chart 3. Alternatively, the entire rate range could be displayed under the Average Rate column. The elapsed time measurement in the first column of FIG. 8A is readily derived by the external monitoring device by dividing the average rate in beats per minute by the number of events counted to determine the corresponding average rate. As noted above, each telemetry transmission includes telemetry of the programmed values of the event counter circuitry, including the information stored on the term bus 204 and on TRINDHIST line 206. This information may be decoded by the external monitoring device in the same fashion as performed by the term decode logic 380 (FIG. 3A) of the implanted device in order to derive the number of events counted per each calculation of average event rate, according to the correspondence between counted events and programmed parameters discussed above. The information in the percentage paced column simply reflects decoding of the 2 bits corresponding to stored percentage paced value (see Chart 2).

This information is presented in a different fashion in FIG. 8B, which illustrates an appropriate display for information stored during histogram storage. This information is displayed in four columns labeled "Rate Bins", "Total Event/Term", "% Total Events", and "% Paced". The first column lists the rate bins corresponding to the first three digits of the random access memory address. The second column reflects the value stored in the random access memory at the address corresponding to the bin code and 0 (events bin). The percent total events is obtained by dividing the value in the total event/term column by the total of all values listed in that column. The values in the percentage paced column are derived as discussed above by dividing the number stored in the percent paced bin by the number stored in the events bin, and using the derived quotient to determine the percentage paced. In the display illustrated, the percentage paced is divided into four percentage paced ranges, as discussed above.

FIG. 8C illustrates information stored by the event counter circuitry during a trend analysis sequence in a graphic format. In this format, the same type of information used to generate the display of FIG. 8 is used to construct a trend line display. In this case, each average rate value is displayed in the form of a box extending from the lower end of the rate range corresponding to the stored bin code to the upper end of the rate range corresponding to the stored bin code, the width of each box corresponding to the time elapsed during counting of the events used to generate the average rate value, calculated as discussed above in conjunction with the display of elapsed time in conjunction with FIG. 8A. Percent paced indicators in this display may be accomplished by variable shading or coloring of the boxes.

FIG. 8D is a graphic representation of the information stored in the context of a histogram storage, and is believed to be self-explanatory. In this display, the total number of beats is displayed on the horizontal axis, with rate ranges on the vertical axis. Percentages illustrated associated with the bars correspond to the values in the percent total event column of FIG. 8B. Total numbers of events are also displayed and are reflected in the length of the bars on the graph and are calculated by multiplying the value stored in the events bin (address=bin code and 0) by the number of events counted calculated average rate value (derived from programmed parameters as discussed above).

The present invention, as described above, provides an extremely flexible, programmable format data storage and telemetry system particularly optimized for use in implantable devices. The system disclosed is capable of storing a significant amount of information regarding the underlying condition of the patient and the operation of the pacemaker in a relatively limited storage space, i.e., a 16×16 bit random access memory rate. This should not be interpreted to suggest that the invention might not be practiced in conjunction with larger size memories, if greater data storage is required.

The data storage method disclosed is particularly optimized for providing a maximum amount of data compression by tying sampling cycles to actual events counted, rather than to predetermined time increments. For example, rather than setting a predetermined time increment and counting all events that occur therein to determine an average rate, the device instead insures that each average taken will include a predetermined number of events. Thus, the calculated values of the average rate of event occurrence and the percentage of paced events are always based upon the same number of events. This is particularly helpful in the context of a cardiac pacemaker, where a decrease in the rate of event occurrence (lower heart rates and pacing rates) allows for data to be gathered over a longer period of time.

However, the basic invention could also usefully be practiced in the context of a system which set predetermined time periods, and counted the events which occurred during those time periods in order to derive the stored average rate values. For example, the timer logic in such case would be programmed to generate the signal initiating the averaging function, and the current count in the event counters would be used in conjunction with the known time interval to derive the average event rate. Such a system is believed to be a useful alternative to the system disclosed in the above application, and does have an advantage in the context of a trend line analysis in that each averaged rate value corresponds to a predetermined known increment of time. Such an embodiment is also believed to be within the scope of the present invention.

The invention disclosed is implemented in the form of full custom digital logic circuitry. However, other approaches to control of timing and sequencing functions may be useful in the context of the present invention, including microprocessor based circuitry.

The disclosed embodiment envisions counting signals in a cardiac pacemaker which correspond to actual contractions of the heart, including signals generated concurrent with pacing pulses and signals detected from the heart. However, the data compression and storage function provided by the event counter logic of the present invention is equally applicable to storage of other event markers and signals which might be generated in an implantable stimulator or monitor. Such markers and signals may include a variety of measurements regarding actual function of the implantable device, such as outputs of one or more sensors, measurements of the amplitudes of detected electrical signals, measurements of the impedance of the electrode system, measurements of battery voltage, and so forth. Indeed, the system is applicable to the storage and display of any parameters associated with operation of any implantable monitor or medical stimulator. The invention will also be useful in the context of external medical monitoring and stimulation devices. However, it is anticipated that in general, greater data storage ability and more lenient size constraints will pertain in the context of external devices. Therefore, while the invention is believed to be useful in the context of external stimulators and other monitoring devices in general, it is believed particularly optimized and particularly useful in the context of implantable medical monitoring and stimulation devices.

As such, the above described embodiment should be considered exemplary, rather than limiting with regard to the following claims.

We claim:

1. In an implantable device of the type comprising means for repeatedly measuring one of more predetermined parameters and memory means for storing information related to the measurements of said parameter for later transmission to an external monitoring device, the improvement wherein:

said measuring means comprises means for providing digital codes indicative of the measurements of said one or more parameters;

wherein said memory means comprises a random access memory capable of storing data at a plurality of addresses, means for initializing said random access memory such that the data at each of said addresses of said random access memory is set to a predetermined value, and memory addressing means for addressing said random access memory and altering the data stored therein; and wherein said memory addressing means operates in first and second alternative modes, such that in said first mode said addressing means sequentially addresses said addresses of said random access memory and sequentially stores said digital codes at successive ones of said addresses within said random access memory and such that in said second mode, said addressing means employs said digital codes to address said addresses of said random access memory, and with each said addressing of said random access memory incremented the value in said random access memory at the one of said addresses corresponding to the said digital code used to address said random access memory.

2. A medical device according to claim 1 wherein said measuring means is adapted to measure a physiologic parameter of the human body.

3. A device according to claim 2 wherein said physiologic parameter measured is the rate of occurrence of physiologic events within the body.

4. A device according to claim 3 wherein said device comprises an electrical stimulator means for generating stimulus pulses and wherein said one or more parameters measured comprise the rate of generation of said stimulus pulses.

5. A medical device according to claim 4 wherein said device takes the form of a cardiac pacemaker having a sensor responsive to the metabolic demand for oxygenated blood and for regulating the rate of generation of said stimulus pulses in response to said demand for oxygenated blood.

6. A device according to claim 5 wherein said one or more measured parameters comprise the repetition rate of contractions of a chamber of the heart and wherein said measuring means further comprises means for measuring the relative numbers of said stimulus pulses and said heart contractions.

7. A medical device according to claim 6 wherein in said first mode, said addressing means operates to sequentially store said measurements indicative of the relative numbers of stimulus pulses and heart contractions, along with said sequentially stored digital codes indicative of said measurements of said one or more parameters.

8. A device according to claim 6 wherein in said second mode said addressing means comprises means for addressing two addresses based on said digital codes and for incrementing the stored value in one of said two addresses, based on said measurement of the relative numbers of said stimulus pulses and said natural contractions of said heart.

9. A medical device according to claim 1 wherein said measuring means comprising means for measuring a physiologic parameter of the human body indicative of metabolic demand for oxygenated blood.

10. An implantable medical device comprising means for measuring the rate of occurrence of recurring physiologic events and storage and telemetry means for storing information related to said rates of said physiologic events, and for telemetering said stored information out of said medical device to an external monitor;

wherein said means for measuring comprises means for counting a predetermined number of said events and for measuring the interval of time required to count said predetermined number of events and for providing digital codes indicative of the average rate of occurrence of said events, wherein said storage and telemetry means comprises means for storing said digital codes and for telemetering said stored event rates out of said storage means in timed order for telemetry to said external monitoring device.

11. An implantable medical device according to claim 10 wherein said device comprises an implantable pacemaker and wherein said recurring physiologic events comprise natural contractions of a chamber of the heart and stimulus pulses generated by said implantable pacemaker, both said natural heart contractions and said stimulus pulses counted in order to reach said predetermined count, wherein said measurement means further comprises means for determining the relative percentage of said events which are counted which correspond to said stimulus pulses compared to the total number of said events counted and for generating further digital codes indicative thereof, wherein said storage means and telemetry means comprises means for storing said further digital codes and for telemetering said further digital codes in time order sequence to said external monitoring means whereby said external monitoring means may display associated event rates and percentage of recorded events corresponding to stimulus pulses.

12. A medical device according to claim 10 or claim 11 further comprising means for telemetering the value of said predetermined count to said external device, along with said stored average rate values whereby said external monitoring device is provided with sufficient information to determine the approximate interval of time over which each of said average rate values was calculated.

* * * * *